(12) United States Patent
Woolf et al.

(10) Patent No.: US 11,983,875 B2
(45) Date of Patent: May 14, 2024

(54) METHOD AND APPARATUS FOR ANALYSING INTRACORONARY IMAGES

(71) Applicant: CAMBRIDGE ENTERPRISE LIMITED, Cambridge (GB)

(72) Inventors: Adam Woolf, Cambridge (GB); Martin Bennett, Cambridge (GB)

(73) Assignee: CAMBRIDGE ENTERPRISE LIMITED, Cambridge (GB)

( * ) Notice: Subject to any disclaimer, the term of this patent is extended or adjusted under 35 U.S.C. 154(b) by 166 days.

(21) Appl. No.: 17/606,996

(22) PCT Filed: Apr. 30, 2020

(86) PCT No.: PCT/GB2020/051051
§ 371 (c)(1),
(2) Date: Oct. 27, 2021

(87) PCT Pub. No.: WO2020/222004
PCT Pub. Date: Nov. 5, 2020

(65) Prior Publication Data
US 2022/0277456 A1 Sep. 1, 2022

(30) Foreign Application Priority Data
May 1, 2019 (GB) .................................. 1906103

(51) Int. Cl.
*G06V 10/764* (2022.01)
*A61B 5/00* (2006.01)
(Continued)

(52) U.S. Cl.
CPC .......... *G06T 7/0016* (2013.01); *A61B 5/0066* (2013.01); *G06V 10/40* (2022.01);
(Continued)

(58) Field of Classification Search
CPC . G06T 2207/10101; G06T 2207/20081; G06T 2207/20084; G06T 2207/30048;
(Continued)

(56) References Cited

U.S. PATENT DOCUMENTS 10,796,781 B2 * 10/2020 Mitra .................... G16B 20/00
11,389,130 B2 * 7/2022 Itu .......................... A61B 6/504
(Continued)

FOREIGN PATENT DOCUMENTS

CN       108961229 A     12/2018
CN       109091167 A     12/2018
(Continued)

OTHER PUBLICATIONS

"International Search Report and Written Opinion of the International Searching Authority", International Application No. PCT/GB2020/051051, dated Oct. 26, 2020, 14 pp.
(Continued)

*Primary Examiner* — Tsung Yin Tsai
(74) *Attorney, Agent, or Firm* — Myers Bigel, P.A.

(57) ABSTRACT

Embodiments of the present techniques provide apparatus and methods for analysing intracoronary images, for example to predict the likelihood of a disease, disease presentation or event, and/or to track performance of a drug or other treatment. The method may comprise: for each image in the set of images of a coronary artery: classifying the image, using a first neural network, for the presence or absence of diseased tissue; when the image is classified as having diseased tissue present, classifying the image, using a second neural network, for the presence or absence of an artefact; determining whether to analyse the image based on the classifying steps; when the image is to be analysed, analysing the image by identifying, using a third neural
(Continued)

network, one or more features of interest in a coronary artery tissue; and measuring each identified feature of interest.

18 Claims, 14 Drawing Sheets

(51) Int. Cl.
| | |
|---|---|
| *G06T 7/00* | (2017.01) |
| *G06V 10/40* | (2022.01) |
| *G06V 10/766* | (2022.01) |
| *G06V 10/774* | (2022.01) |
| *G06V 10/82* | (2022.01) |
| *G16H 30/20* | (2018.01) |

(52) U.S. Cl.
CPC .......... *G06V 10/764* (2022.01); *G06V 10/766* (2022.01); *G06V 10/774* (2022.01); *G06V 10/82* (2022.01); *G16H 30/20* (2018.01); *A61B 2576/00* (2013.01); *G06T 2207/10101* (2013.01); *G06T 2207/20081* (2013.01); *G06T 2207/20084* (2013.01); *G06T 2207/30048* (2013.01); *G06T 2207/30101* (2013.01); *G06T 2207/30168* (2013.01); *G06V 2201/03* (2022.01)

(58) Field of Classification Search
CPC . G06T 2207/30101; G06T 2207/30168; G06T 7/0012; G06T 7/0016; A61B 2576/00; A61B 5/0066; G06V 10/40; G06V 10/764; G06V 10/766; G06V 10/774; G06V 10/82; G06V 2201/03; G16H 30/20
See application file for complete search history.

(56) References Cited

U.S. PATENT DOCUMENTS

| | | | |
|---|---|---|---|
| 2011/0190650 A1* | 8/2011 | McNair | A61B 5/6898 600/518 |
| 2012/0003228 A1* | 1/2012 | Smith | A61P 29/00 435/7.1 |
| 2014/0276011 A1 | 9/2014 | Schmitt et al. | |
| 2016/0267324 A1* | 9/2016 | Shoaib | H04N 1/00204 |
| 2017/0148158 A1 | 5/2017 | Najarian et al. | |
| 2017/0161428 A1* | 6/2017 | Mitra | G16B 20/00 |
| 2017/0309018 A1 | 10/2017 | Shalev et al. | |
| 2018/0310888 A1* | 11/2018 | Itu | G16H 50/50 |
| 2018/0368781 A1* | 12/2018 | De Man | A61B 5/055 |
| 2019/0336096 A1* | 11/2019 | Itu | G16H 50/50 |
| 2020/0185084 A1* | 6/2020 | Syeda-Mahmood | G06V 10/7515 |
| 2020/0187790 A1* | 6/2020 | Milner | G06F 18/2411 |
| 2022/0277456 A1* | 9/2022 | Woolf | G06V 10/766 |

FOREIGN PATENT DOCUMENTS

| | | | |
|---|---|---|---|
| WO | 2013144912 | A1 | 10/2013 |
| WO | 2017214421 | A1 | 12/2017 |

OTHER PUBLICATIONS

"Patents Act 1977: Search Report under Section 17(5)", GB Application No. GB1906103.5, dated Oct. 30, 2019, 3 pp.

Fujii, Kenichi, et al., "OCT Assessment of Thin-Cap Fibroatheroma Distribution in Native Coronary Arteries", JACC: Cardiovascular Imaging, vol. 3, No. 2, Feb. 10, 2010, pp. 168-175.

Gessert, Nils, et al., "Automatic Plaque Detection in IVOCT Pullbacks Using Convolutional Neural Networks", arxiv.org, Cornell University Library, 201 Olin Library Cornell University, Ithaca, NY 14853 XP081179222, DOI: 10.1109/TMI.2018.2865659, Aug. 13, 2018, 9 pp.

Girshick, Ross, "Fast R-CNN", 2015 IEEE International Conference on Computer Vision (ICCV), Santiago, Chile, Dec. 7, 2015, pp. 1440-1448.

Kawasaki, Masanori, et al., "Tissue Characterization of Coronary Plaques and Assessment of Thickness of Fibrous Cap Using Integrated Backscatter Intravascular Ultrasound", Circulation Journal, vol. 74, Issue 12, Dec. 2010, pp. 2641-2648.

Larsen, Anders Boesen Lindbo, et al., "Autoencoding beyond pixels using a learned similarity metric", Retrieved Jun. 9, 2017 from the Internet: URL:https://arxiv.org/pdf/1512.09300.pdf, Feb. 10, 2016, 8 pp.

Rico-Jimenez, Jose J., et al., "Automatic classification of atherosclerotic plaques imaged with intravascular OCT", Biomedical Optics Express, vol. 7, No. 10, Oct. 1, 2016, pp. 4069-4085.

Ripatti, Samuli, et al., "A multilocus genetic risk score for coronary heart disease: case-control and prospective cohort analyses", The Lancet, vol. 376, Oct. 23, 2010, pp. 1393-1400.

Tearney, Guillermo J., et al., "Consensus Standards for Acquisition, Measurement, and Reporting of Intravascular Optical Coherence Tomography Studies", Journal of the American College of Cardiology, vol. 59, No. 12, Mar. 20, 2012, pp. 1058-1072.

Thanassoulis, George, et al., "A Genetic Risk Score Is Associated With Incident Cardiovascular Disease and Coronary Artery Calcium The Framingham Heart Study", Circulation: Cardiovascular Genetics, vol. 5, No. 1, Jan. 10, 2012, pp. 113-121.

Virmani, Renu, et al., "Lessons From Sudden Coronary Death A Comprehensive Morphological Classification Scheme for Atherosclerotic Lesions", Arteriosclerosis, Thrombosis, and Vascular Biology, vol. 20, No. 5, May 2000, pp. 1262-1275.

Virmani, Renu, et al., "Vulnerable Plaque: The Pathology of Unstable Coronary Lesions", Journal of Interventional Cardiology, vol. 15, No. 6, Dec. 2002, pp. 439-446.

Xie, Yong, et al., "Clinical Outcome of Nonculprit Plaque Ruptures in Patients With Acute Coronary Syndrome in the Prospect Study", JACC: Cardiovascular Imaging, vol. 7, No. 4, Apr. 1, 2014, pp. 397-405.

Zahnd, Guillaume, et al., "Contour segmentation of the intima, media, and adventitia layers in intracoronary OCT images: application to fully automatic detection of healthy wall regions", International Journal of Computer Assisted Radiology and Surgery, vol. 12, No. 11, Aug. 11, 2017, pp. 1923-1936.

Zahnd, Guillaume, et al., "Quantification of fibrous cap thickness in intracoronary optical coherence tomography with a contour segmentation method based on dynamic programming", International Journal of Computer Assisted Radiology and Surgery, vol. 10, No. 9, Mar. 5, 2015, pp. 1383-1394.

* cited by examiner

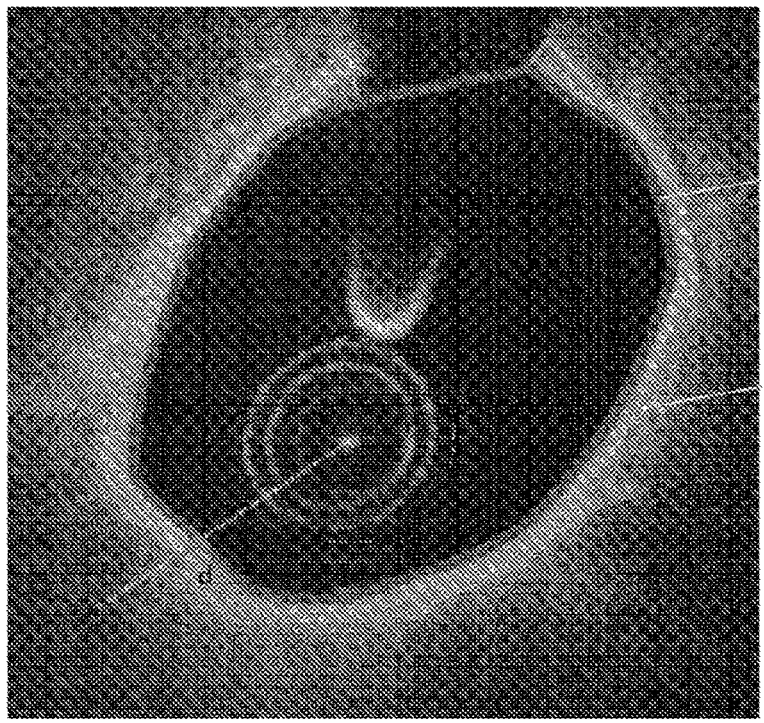
Fig 2e
Fig 2f
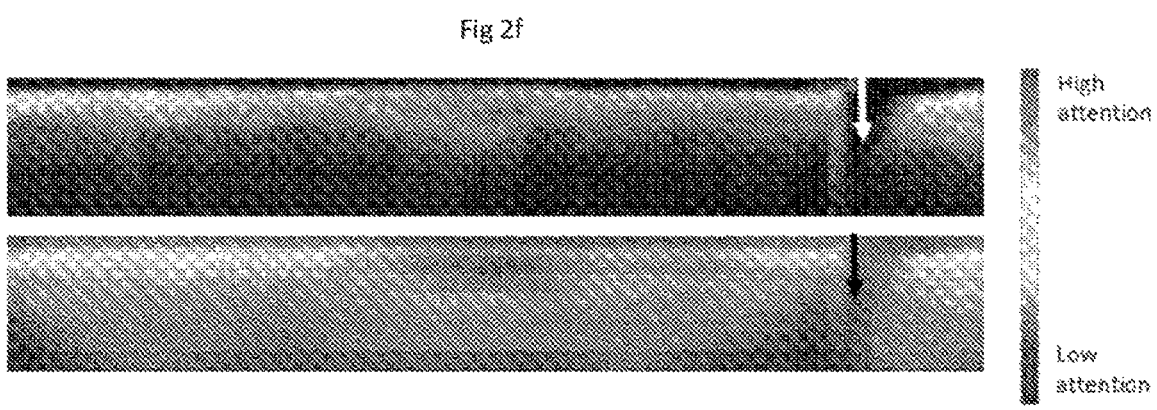
Fig 2g

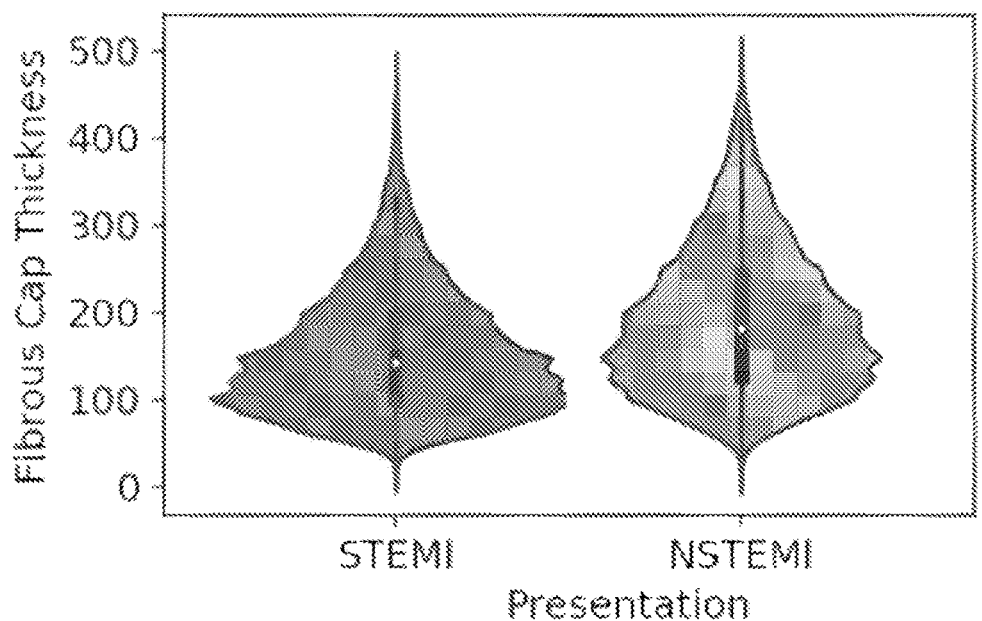
Fig 5a
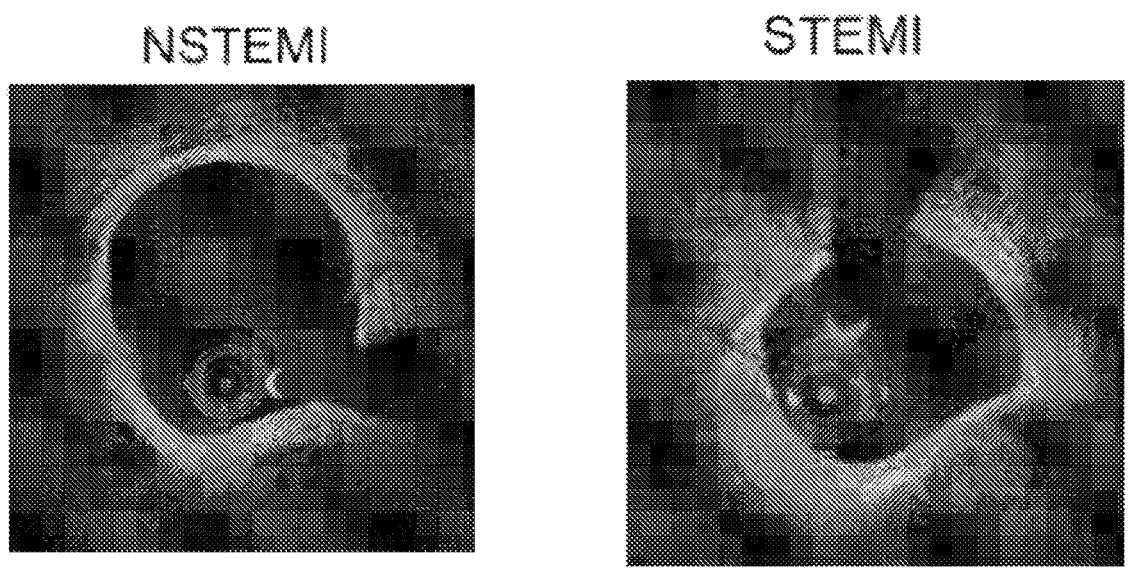
Fig 5b
Fig 5c

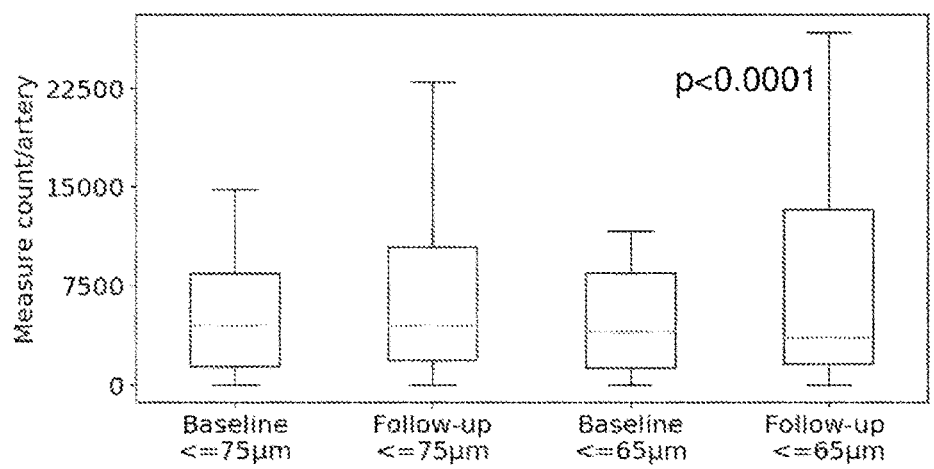
Fig 9a
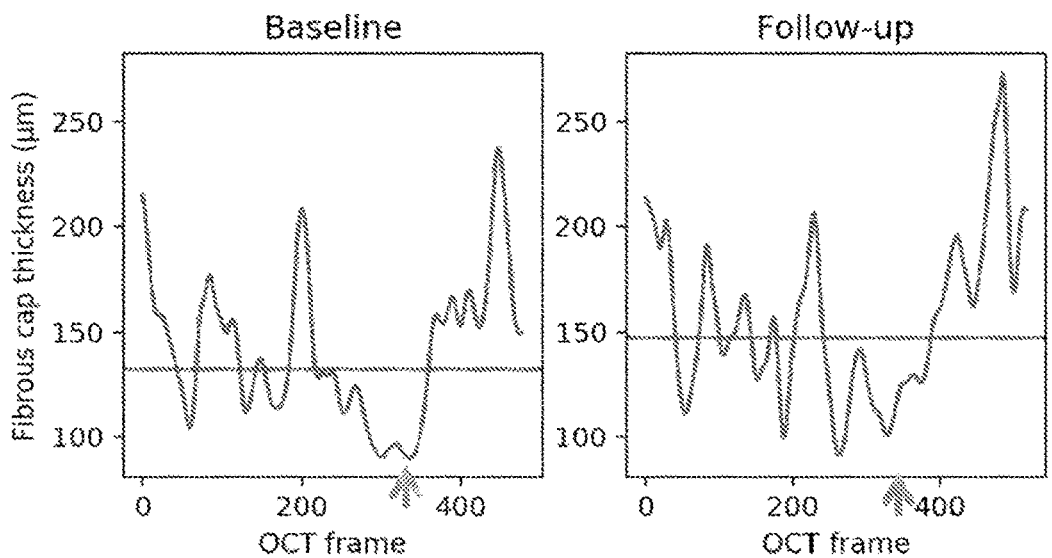
Fig 9b
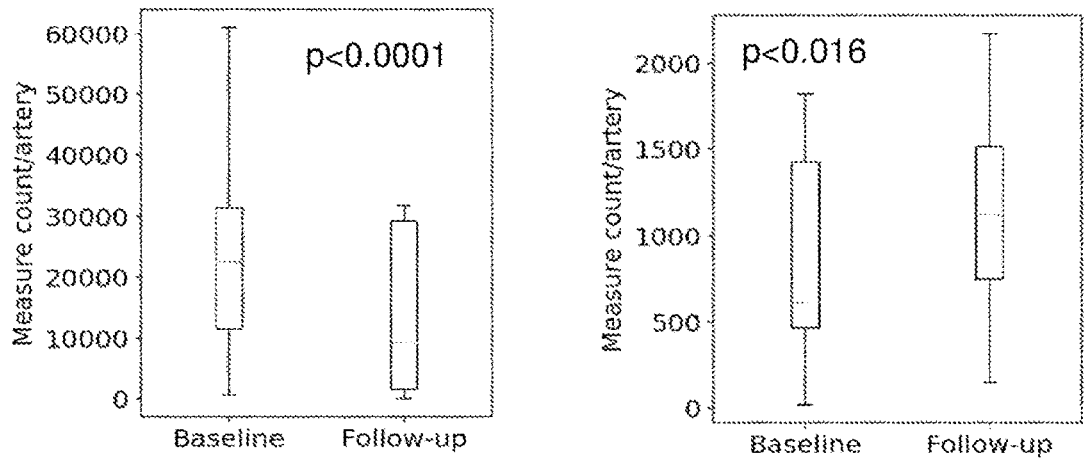
Fig 9c
Fig 9d

METHOD AND APPARATUS FOR ANALYSING INTRACORONARY IMAGES

RELATED APPLICATIONS

This application is a 35 U.S.C. § 371 national stage application of PCT Application No. PCT/GB2020/051051, filed on Apr. 30, 2020, which claims priority from Great Britain Patent Application No. 1906103.5, filed on May 1, 2019, the contents of which are incorporated herein by reference in their entireties. The above-referenced PCT International Application was published in the English language as International Publication No. WO 2020/222004 A1 on Nov. 5, 2020.

FIELD

The application relates to a method and apparatus for analysing intracoronary images, for example to predict the likelihood of a disease, disease presentation or event, and/or to track performance of a drug or other treatment.

BACKGROUND

Despite its prevalence, prediction of clinical events in coronary artery disease (CAD) is typically based on population demographics. More recently such predictions may have superimposed genetic risk scores, for example as described in "Multilocus genetic risk score for coronary heart disease: case-control and prospective cohort analyses" by Ripattis et al published in Lancet 376, 1393-1400 (2010) or "A genetic risk score is associated with incident cardiovascular disease and coronary artery calcium: the Framingham Heart Study" by Thanassoulis et al published in Circ. Cardiovasc. Genet. 5, 113-21 (2012).

High-resolution intracoronary imaging may be used to capture patient-specific features for individualized risk-prediction, but requires clinician interpretation. For example, intracoronary imaging has been used to provide patient-specific data on the extent and type of atherosclerosis as described in "Clinical outcome of nonculprit plaque ruptures in patients with acute coronary syndrome in the PROSPECT study" by Xie et al published in JACC Cardiovasc Imaging 7, 397-405 (2014). However, as reported, less than 20% of 'high-risk' atherosclerotic plaques identified on natural history studies resulted in patient events over 5 years. Poor performance may be due to multiple factors, including unvalidated high-risk imaging features, clinician interpretation with poor inter-observer reproducibility, imaging artefacts, and low spatial resolution.

Another use of high-resolution imaging such as optical coherence tomography (OCT) is described in "Tissue characterization of coronary plaques and assessment of thickness of fibrous cap using integrated backscatter intravascular ultrasound. Comparison with histology and optical coherence tomography" by Kawasaki et al published in Circ J 74, 2641-2648 (2010)". OCT is used to visualise tissue components and identify different plaque types. However, massive imaging datasets are produced and only small regions of disease are selected for detailed clinician interpretation. Attempts have been made towards automation as described in "Quantification of fibrous cap thickness in intracoronary optical coherence tomography with a contour segmentation method based on dynamic programming" by Zahnd et al published in Int J Comput Assist Radiol Surg 10, 1383-1394 (2015) or "Contour segmentation of the intima, media, and adventitia layers in intracoronary OCT images: application to fully automatic detection of healthy wall regions by Zahnd et al published in Int J Comput Assist Radiol Surg (2017). doi:10.1007/s11548-017-1657-7. However, as explained in these articles, both the frequency and variety of artefacts seen in clinical practice mean that even semi-automated analysis requires region selection and interpretation by clinicians, or limited analysis on perfect coronary anatomy.

Background information can be found in: US2014/0276011 which describes a method and apparatus of automatically locating in an image of a blood vessel the lumen boundary at a position in the vessel and from that measuring the diameter of the vessel; US2017/309018 which describes methods and apparatus for automatically classifying intravascular plaque using features extracted from intravascular OCT imagery; CN108961229 which describes a method and system for detecting a vulnerable plaque from a cardiovascular OCT image based on deep learning; and CN109091167 which describes a method for predicting growth of coronary atherosclerotic plaque. Further background information can be found in US2017/0148158 which describes systems and techniques to analyse angiogram image data in order to extract vasculature information, where angiography involves obtaining X-ray images of contrast dye flowing through vasculature to visualise the inside, or lumen, of blood vessels and organs.

The present applicant has recognised the need for a new automated method of analysing high-resolution intracoronary imaging.

SUMMARY

According to the present invention there is provided an apparatus and method as set forth in the appended claims. Other features of the invention will be apparent from the dependent claims, and the description which follows.

We describe an automated computer-implemented method for analysing a set of images of a coronary artery, the method comprising: for each set of three images in the set of images: classifying the image set, using a first neural network, for the presence or absence of diseased tissue; when the set is classified as having diseased tissue present, classifying the set, using a second neural network, for the presence or absence of an artefact; determining whether to analyse the image based on the classification; and when the image is analysed: analysing the image, using a third neural network, by identifying one or more features of interest in a coronary artery tissue; and measuring each identified feature of interest.

We also describe an apparatus for analysing a set of images of a coronary artery, the apparatus comprising: an imaging device for capturing a set of images of a coronary artery; and at least one processor, coupled to memory, arranged to: for each image in the set of images: classify the image, using a first neural network, for the presence or absence of diseased tissue; when the image is classified as having diseased tissue present, classify the image, using a second neural network, for the presence or absence of an artefact; determine whether to analyse the image based on the classification; and when the image is analysed: analyse the image, using a third neural network, to identify one or more features of interest in a coronary artery tissue; and measure each identified feature of interest.

Such an automated method or apparatus may be free from operator engagement after image acquisition and may thus be applicable to a wide range of datasets. The set of images may be a full or partial pullback.

Prior to classifying the image, the coronary artery in the image may be sampled into a plurality of samples. A set of samples, e.g. three samples, may be input into a version of the second neural network for classifying the image, but trained on samples. Each sample may be a rectangular segment and may have a top edge aligned with a lumen edge of the artery.

Classifying the image using the second neural network may comprise determining a proportion of coronary artery tissue which is detectable in each sample in the input set; and classifying the image based on the determined proportion. The second neural network may classify the image by analysing a plurality of training dataset samples using a supervised learning algorithm. Classifying the image may comprise classifying any present artefact as correctable or non-correctable, for example based on whether any underlying tissue was detected. A correctable artefact may be generated by a focal artefact (e.g. focal luminal residual blood and resultant focal tissue shadow) or an arterial architectural component (e.g. intervening outcrop of arterial tissue between the imaging device (e.g. OCT catheter) and the region of interest, i.e. as seen where an OCT catheter lies partially within a branch/bifurcation) and a non-correctable artefact may be generated by a medical architectural component (e.g. a stent, the guide catheter). There is abundant data from repeat patient pullbacks which generates both artefact-rich and artefact-free comparison states for training. For example, the image may be classified as having a correctable artefact when the determined proportion of observable tissue is over 50% but less than 100%, i.e. at least half the sample shows underlying tissue. The image may be classified as having a non-correctable artefact when the determined proportion is around 0%, i.e. virtually none of the sample shows underlying tissue.

When the image comprises a correctable artefact, the method may further comprise correcting an image classified as having a correctable artefact before analysing the image. Correcting an image may comprise applying a variational-autoencoder generative adversarial network to the identified image to recover detail of the coronary artery tissue underneath the identified artefact. For example, the network may generate replacement samples to be inserted in the image. Where replacement samples may not be generated, the sample may be classified as comprising a non-correctable artefact.

When the image is classified as having an absence of diseased tissue, the image may be replaced with blank information. Thus the same number of inputs is retained as the set of images.

Measuring each identified feature of interest may comprise measuring any one or more of: fibrous cap/tissue thickness, fibrous tissue pixel intensity and thickness, plaque composition, lumen area, and diseased lumen circumference.

The method may further comprise, prior to analysing the image, sampling the coronary artery in the image into a plurality of samples around the lumen; and arranging the samples in a linear representation of the coronary artery. The sampling may be the same as the sampling described above. Analysing the processed image may further comprise: identifying, using a regression bounding box technique, an interface between fibrous tissue and necrotic or calcific tissue in each of the plurality of samples. Measuring the identified feature of interest may comprise measuring the distances between the interface and an edge of the sample and the lumen edge and the edge of the sample to determine the distance between the interface and the lumen edge, i.e. to determine the thickness of the fibrous tissue. A fibrous cap may be defined as fibrous tissue overlying necrotic/lipid tissue. For this subset of fibrous tissue, the measurement may be the thickness of the fibrous cap.

The images of coronary arteries may be optical coherence tomography images.

There may be many applications of the analysis. For example, the method may further comprise determining, for example using a fourth neural network, the likelihood of the patient presenting with a particular manifestation of coronary artery disease or having an acute cardiac event (e.g. heart attack) in the near future, using the measurement of each identified feature of interest, which may be fibrous tissue overlying necrotic core/lipid, or calcium. The coronary artery disease may be stable angina, non-ST elevation myocardial infarction (NSTEMI) or ST elevation myocardial infarction (STEMI). Such a fourth neural network may be an independent series classifier. The fourth neural network may receive as inputs the measurement of each identified feature of interest for each analysed image and blank information for each image which is not analysed. The only input(s) are the measurement(s) and any blank information and thus the determination is identifying patient presentation independent of original patient or pullback context or confounding post-event findings. This produces predictions based on unbiased data, e.g. by removing any bias caused by operator measurement and/or bias from the context of the artery inputs, e.g. due to presentation-related artefacts.

Another application is to determine variations in the coronary artery over time, e.g. in response to drug and/or other treatments or as a study (natural history) of the coronary artery. The images or set of images may comprise a first set or subset of images of a coronary artery of a patient at a first stage (e.g. a first stage in the treatment) and at least a second set or subset of images of the coronary artery of the patient at, at least, a second, subsequent stage. It will be understood that images of a patient may be obtained/captured at more than two stages or points in time, and therefore, the images or set of images may comprise images of the patient at a first stage, a second stage, a third stage, a fourth stage, and so on. The first subset of images of a patient at a first stage may be captured at a first time (e.g. a first stage or first point in time in the treatment), and the second subset of images may be captured at, at least, a second time (e.g. a second, third, fourth or subsequent stage, or second, third, fourth or subsequent point in time in the treatment).

The method may further comprise: measuring a first set of measurements for each identified feature of interest for the first set (or subset) of images; measuring at least a second set of measurements for each identified feature of interest for the at least second set (or subset) of images; and determining, using the first and at least second sets of measurements, any change in the coronary artery, e.g. which may relate to the efficacy of the treatment where a treatment is applied. Thus, the first time is a first stage in treatment and the second time is a second stage in the treatment. It will be understood that the determining step may be performed using any number of sets of measurements, using images captured at any time/stage. For example, sets of images of a patient's coronary artery may be captured at the start of a treatment process, at one or more intermediate points during the treatment process, and at the end of a treatment process. Any two or more of these sets of images (or the sets of measurements associated with the images) may be compared to determine a change in the coronary artery. For example, the sets of images at the start and end of the treatment may be compared, or at the start and an intermediate point, or the intermediate point and the end, or between intermediate points, or between the start, each intermediate point and the end. It will be understood that any two or more sets or subsets of images captured at any two or more points in time may be used to determine any change in the coronary artery.

Another application is a method of diagnosis of a patient comprising: receiving a plurality of images of a coronary artery of the patient; for each of the received images: classifying the image, using a first neural network, for the presence or absence of diseased tissue; when the image is classified as having diseased tissue present, classifying the image, using a second neural network, for the presence or absence of an artefact; determining whether to analyse the image based on the classification; and when the image is analysed: analysing the processed image, using a third neural network, to identify an interface between fibrous tissue and necrotic, lipid or calcific tissue; measuring a fibrous tissue or cap thickness; and diagnosing the patient based on the measured fibrous tissue/cap thickness. For example, the diagnosing may be done using a fourth neural network, e.g. one trained on measurements from patients with one or more cardiac diseases.

Another application is a method of treatment of a patient comprising diagnosing a patient with one or more cardiac diseases (e.g. stable angina, non-ST elevation myocardial infarction (NSTEMI) or ST elevation myocardial infarction (STEMI)) and treating the patient based on the diagnosis. Similarly, another application is a method of treatment of a patient predicted to have a high likelihood of a particular cardiac disease and treating the patient based on the prediction.

As will be appreciated by one skilled in the art, the present invention may be embodied as a system, method or computer program product. Accordingly, the present invention may take the form of an entirely hardware embodiment, an entirely software embodiment, or an embodiment combining software and hardware aspects.

Furthermore, the present invention may take the form of a computer program product embodied in a computer readable medium having computer readable program code embodied thereon. The computer readable medium may be a computer readable signal medium or a computer readable storage medium. A computer readable medium may be, for example, but is not limited to, an electronic, magnetic, optical, electromagnetic, infrared, or semiconductor system, apparatus, or device, or any suitable combination of the foregoing.

Computer program code for carrying out operations of the present invention may be written in any combination of one or more programming languages, including object oriented programming languages and conventional procedural programming languages. Code components may be embodied as procedures, methods or the like, and may comprise sub-components which may take the form of instructions or sequences of instructions at any of the levels of abstraction, from the direct machine instructions of a native instruction set to high-level compiled or interpreted language constructs.

Embodiments of the present invention also provide a non-transitory data carrier carrying code which, when implemented on a processor, causes the processor to carry out any of the methods described herein.

The present invention further provides processor control code to implement the methods described herein, for example on a general-purpose computer system or on a digital signal processor (DSP). The present invention also provides a carrier carrying processor control code to, when running, implement any of the methods described herein, in particular on a non-transitory data carrier. The code may be provided on a carrier such as a disk, a microprocessor, CD- or DVD-ROM, programmed memory such as non-volatile memory (e.g. Flash) or read-only memory (firmware), or on a data carrier such as an optical or electrical signal carrier. Code (and/or data) to implement embodiments of the techniques described herein may comprise source, object or executable code in a conventional programming language (interpreted or compiled) such as python, C, or assembly code, code for setting up or controlling an ASIC (Application Specific Integrated Circuit) or FPGA (Field Programmable Gate Array), or code for a hardware description language such as Verilog (RTM) or VHDL (Very high speed integrated circuit Hardware Description Language). As the skilled person will appreciate, such code and/or data may be distributed between a plurality of coupled components in communication with one another. The present invention may comprise a controller which includes a microprocessor, working memory and program memory coupled to one or more of the components of the system.

It will also be clear to one of skill in the art that all or part of a logical method according to embodiments of the present invention may suitably be embodied in a logic apparatus comprising logic elements to perform the steps of the above-described methods, and that such logic elements may comprise components such as logic gates in, for example a programmable logic array or application-specific integrated circuit. Such a logic arrangement may further be embodied in enabling elements for temporarily or permanently establishing logic structures in such an array or circuit using, for example, a virtual hardware descriptor language, which may be stored and transmitted using fixed or transmittable carrier media.

In an embodiment, the present invention may be implemented using multiple processors or control circuits. The present invention may be adapted to run on, or integrated into, the operating system of an apparatus.

In an embodiment, the present invention may be realised in the form of a data carrier having functional data thereon, said functional data comprising functional computer data structures to, when loaded into a computer system or network and operated upon thereby, enable said computer system to perform all the steps of the methods described herein.

BRIEF DESCRIPTION OF THE DRAWINGS

For a better understanding, and to show how embodiments may be carried into effect, reference will now be made, by way of example only, to the accompanying diagrammatic drawings in which:

FIG. 1b is a schematic block diagram of a system for capturing and analysing the multiple images of FIG. 1a;

FIG. 1c is a flowchart of a method for capturing and analysing the multiple images of FIG. 1a;

FIG. 2b is a schematic illustration of the unfolding of the arterial wall of FIG. 2a;

FIG. 2e shows the information which is measured overlaid on FIG. 2a;

FIG. 2f is a horizontal plot of an average value for an arterial region captured using the method of FIG. 1a;

FIG. 2g is an attention map the same arterial region as FIG. 2f;

FIGS. 3b, 3c and 3d are images taken at three locations on the artery in FIG. 3a;

FIG. 5a is a violin plot of fibrous cap thickness (FCT) for NSTEMI and STEMI patients;

FIGS. 5b and 5c are images of a cross-section through an artery of a patient presenting with NSTEMI and STEMI, respectively;

FIG. 6b is a histological section of the fibroatheroma co-registered with FIG. 6a;

FIG. 9a shows boxplots of measurement frequency of FCT at different thickness thresholds between a pre-treatment baseline and post-treatment follow-up;

FIG. 9b shows a single patient's frame-wise plots of FCT between the pre-treatment baseline and post-treatment follow-up;

FIG. 9c shows a boxplot of frequency of lipid between the pre-treatment baseline and post-treatment follow-up; and FIG. 9d shows a boxplot of frequency of calcification between the pre-treatment baseline and post-treatment follow-up.

DETAILED DESCRIPTION OF THE DRAWINGS

Figure 1A:
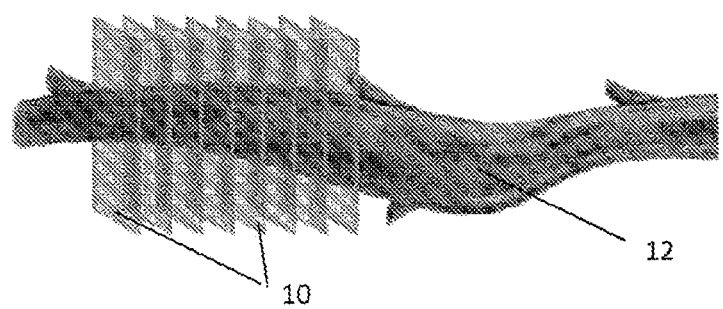
FIG. 1a is a schematic illustration of multiple images of an artery being captured.

FIG. 1a illustrates an artery 12 from which a plurality of images 10 (also termed a set of images or image frames) have been captured. As shown, the images 10 are captured at regular intervals along the length of the artery 12. It will be appreciated that the number of images is merely illustrative and that the images may be captured along all or part of the length of the artery. The set may thus represent a whole or partial pullback along the length of the artery. Furthermore, the spacing between images may be varied as required.

Figure 1B:
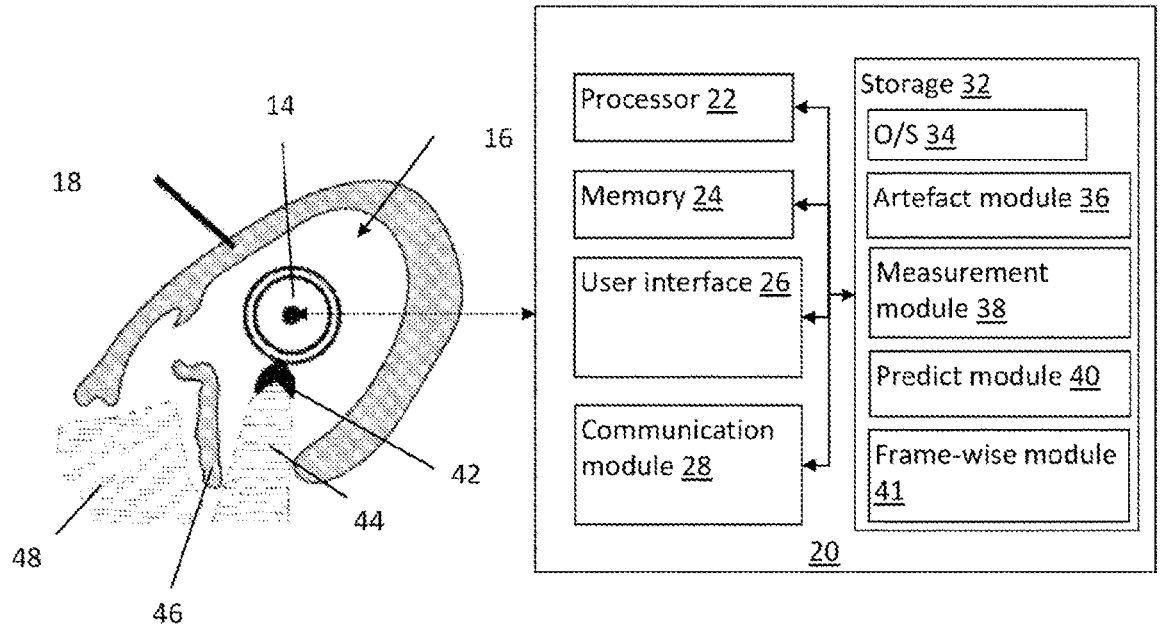

FIG. 1b schematically illustrates a system for capturing and processing an image captured from the artery. Such an image may be captured using an optical coherence tomography (OCT) device 14 which is inserted within the lumen 16 of the artery and images are captured as the device 14 is pulled back through the artery. For example, a pullback with a speed of 20 mm/s lasts about 2.5 seconds and allows imaging of about 72 mm of vessel. As explained in more detail below, the system may be used to analyse the thickness of the plaque region 18 which coats the inner wall of the artery. As schematically illustrated, atherosclerotic plaques are typically eccentric and vary in composition, which may make visualisation of tissue features difficult. The OCT device 14 comprises a guide catheter 42 which prevents OCT information being captured in the shadow region 44 of the catheter 42. Furthermore, as explained in more detail below, there may be one or more artefacts 46 which also prevent OCT information being captured in the shadow region 48 of the artefact. The OCT frames may be captured using standard techniques, e.g. using near-infrared light with wavelengths of between 1250 to 1350 nm, for example as described in "Consensus standards for acquisition, measurement, and reporting of intravascular optical coherence tomography studies: a report from the International Working Group for Intravascular Optical Coherence Tomography Standardization and Validation" by Tearney et al published in. J. Am. Coll. Cardiol. 59, 1058-1072 (2012).

The captured images may be processed or analysed at a separate analysis device 20 which may be remote, e.g. in a different location to the OCT device 14 or may be at least partially local to the OCT device 14 (e.g. located adjacent a patient). Using a remote analysis device 20 may allow access to more powerful resources so that the raw data may be processed more quickly. A local processor has the advantage that it can be used in areas without any wireless connections. Accordingly, both local and remote processing may occur. The analysis device 20 may be implemented in hardware e.g. as a computing device such as a server or may be implemented in the cloud.

The analysis device 20 may comprise standard components such as a processor 22, a user interface 24, storage 26 and a communications interface 28. The user interface 24 may be any standard interface, including a touch sensitive display screen, voice input, keyboard input etc. Similarly, the storage 26 may be conventional memory which may include RAM and/ROM. The communication may be via any suitable protocol, e.g. Wi-Fi, Bluetooth, or a wired connection.

The analysis device 20 further comprises storage 32 for storing modules which are to be carried out on the device. For example, the storage 32 may comprise an operating system module 34 to enable the device to operate. The storage 32 may also comprise an artefact module 36 which may be used to remove artefacts from the image as explained below. There may also be a measurement module 38 for determining or obtaining the interface between the plaque region (e.g. fibrous tissue layer) and the underlying layer as described below. There is also a predict module 40 which uses the measurements from the measurement module to make various predictions as described below. There may also be a frame-wise module 41 which is used to classify each frame as described below. Each of the artefact module 36, the measurement module 38, the predict module 40 and frame-wise module may be implemented as a neural network or other appropriate artificial intelligence system, and each is able to operate independently of the others where appropriate inputs are provided. In other words, the inputs need not be from the peer neural networks but may be other products or may produce independent useful final output.

Figure 1C:
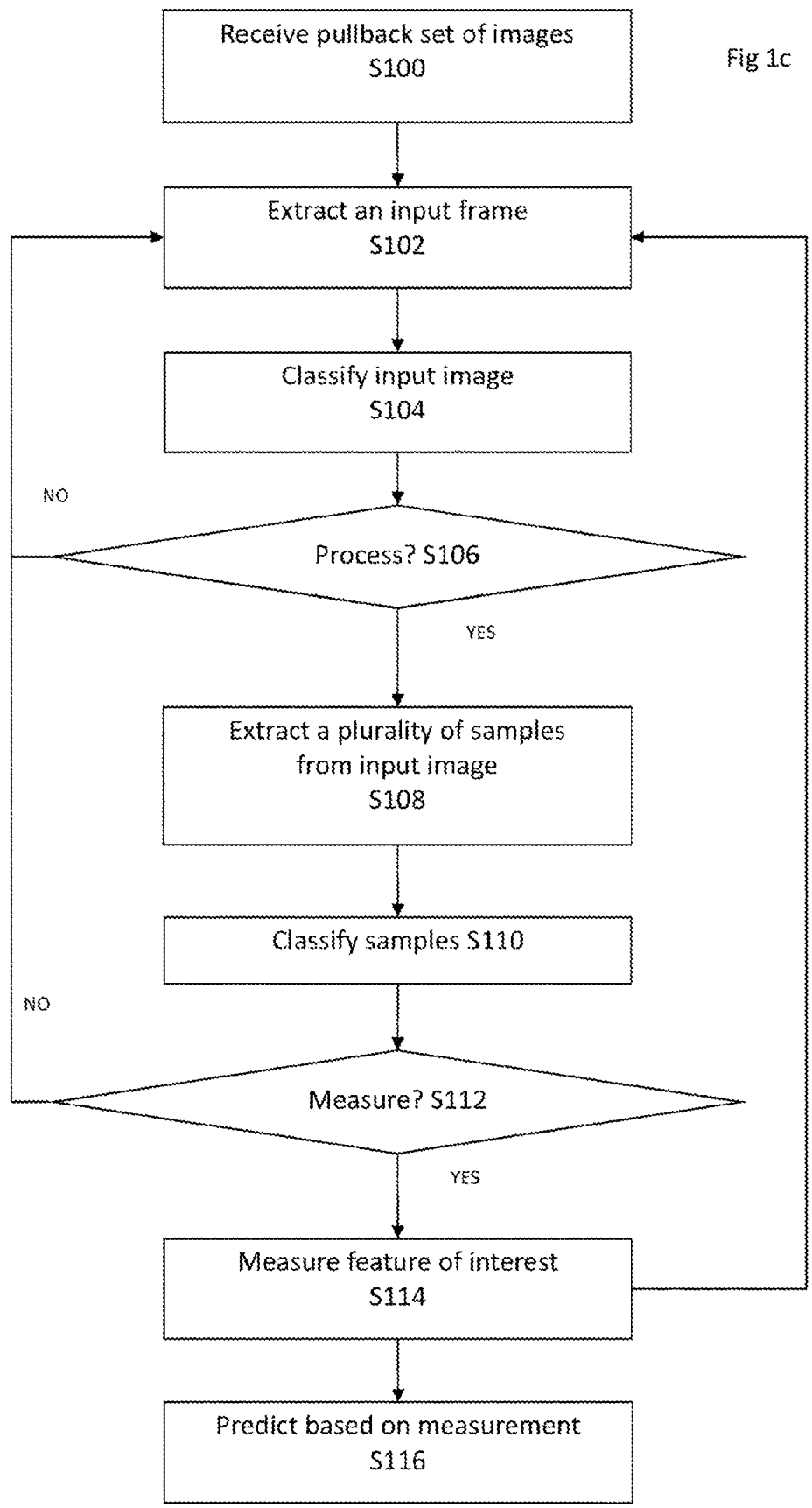
Figure 2A:
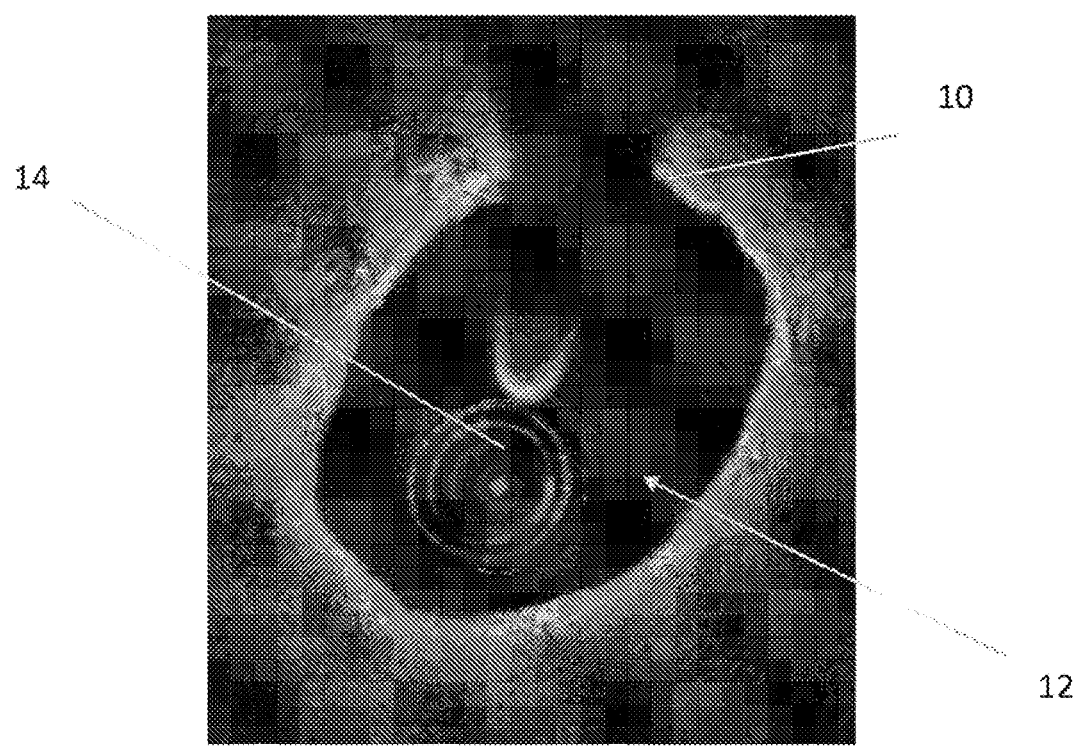
FIG. 2a is an example image frame of an arterial wall captured by the system of FIG. 1b.

The system in FIG. 1*b* may be considered to be a fully independent modular multi-metric autoanalysis system for OCT-based coronary atherosclerotic plaque analysis using deep neural networks. The three tools which are used to analyse the OCT images are the artefact module (may also be termed an artefact identifier), a measurement module and a predict module (which may also be termed a presentation predictor). As described in more detail below, the input includes a whole artery pullback which is analysed to generate micron-level measurement and context-free classification. FIG. 1*c* shows a method for processing or analysing an image which may be implemented using the system above. In a first step (S100), an input pullback set of images is received. The image may be acquired from an imaging system which is within a patient's artery as described above. The set of images may comprise a standard number of images taken along a section of the patient's artery, e.g. for some known device this is 270 images although it will be appreciated that this is merely an exemplary number. A single frame such as the one shown in FIG. 2*a* which shows an image of the wall 10 of the artery 12 captured by an OCT device 14 may then be extracted from the set of images (step S102). Typically, OCT images are captured as grey scale but may have a false colouring applied to the image to make it easier for clinicians to review the image. For example, in this image, there is an orange colour applied to the image and this is just a particular OCT provider's choice rather than a standard. Other OCT providers always produce grey OCT frames.

There may then be an optional initial frame wise classification of the input image to place the image in one of three categories: disease present, disease absent (i.e. healthy) or gross artefact (i.e. artefact across the whole frame). A gross artefact may be result from a large 'architectural' artefact such as a stent and/or guide catheter. The initial frame wise classification may be performed by a neural network which has been appropriately trained. Such an initial frame wise classification may serve as a screening step and may find dominant frame components which may appear as disease and may cause false measurements in subsequent processing if they are included. Such gross artefacts may be easier to identify in the larger context of the whole frame rather than the after applying the sampling described below. The frame wise classifier may accept frames in groups of three.

The frame-wise classification may also relate to the nature of the disease. For example, the samples may also be classified as representing a disease which is not of interest, e.g. pathological intimal thickening where there is no separate fibrous tissue overlay. The frames which are classified in this way may be under the umbrella classification of "healthy". Alternatively, such frames may be identified when attempts to measure information in the frames is undertaken as described below. If the attempt fails, e.g. because there is no tissue-tissue interface (i.e. fibrous tissue and necrotic tissue), the frame (or a sample within the frame) may be classified under this classification.

The frame wise classification is then used to determine whether or not to process the frame further (step S106). If no further processing of a frame is required, the method may loop back to step S102 to consider another input frame in the set of frames. For example, a frame which has been classified as healthy or a frame which has been classified as having a gross artefact may not be processed further because they both may be considered to have no useful information. However, there may be requirement that three consecutive frames are classified as healthy before such frames are not processed further. Such frames which are not processed further may be considered to be disregarded or discarded. However, these discarded frames may be represented as blank spaces, when the set of frames is input into the final prediction stage. Accordingly, the inputs to the predict module are all the same longitudinal dimension regardless of disease extent. Identifying which frames do not contain disease may be useful for efficiency/speed, i.e. subsequent processing, such as measuring features, may be undertaken only for those sequences of frames with disease rather than the whole pullbacks. There may also be other tangential uses of these gross classifications such as labelling frames to display to the clinician. Furthermore, an image which is identified as having a dominant architectural feature such as a stent, catheter or branch/bifurcation may be useful for aligning pullbacks from the same artery taken at different times, e.g. before and three months after stent insertion.

Figure 2B:
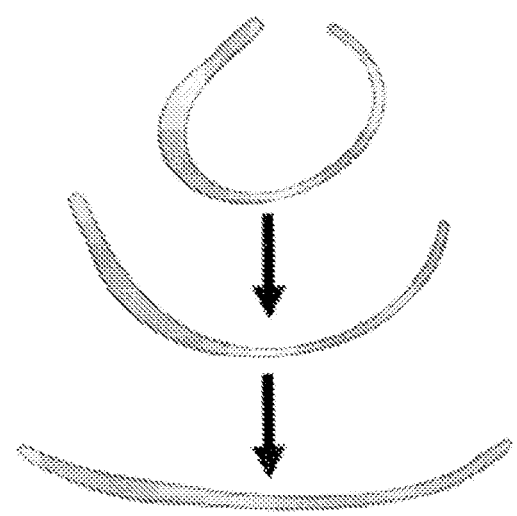
Figures 2C, 2D:
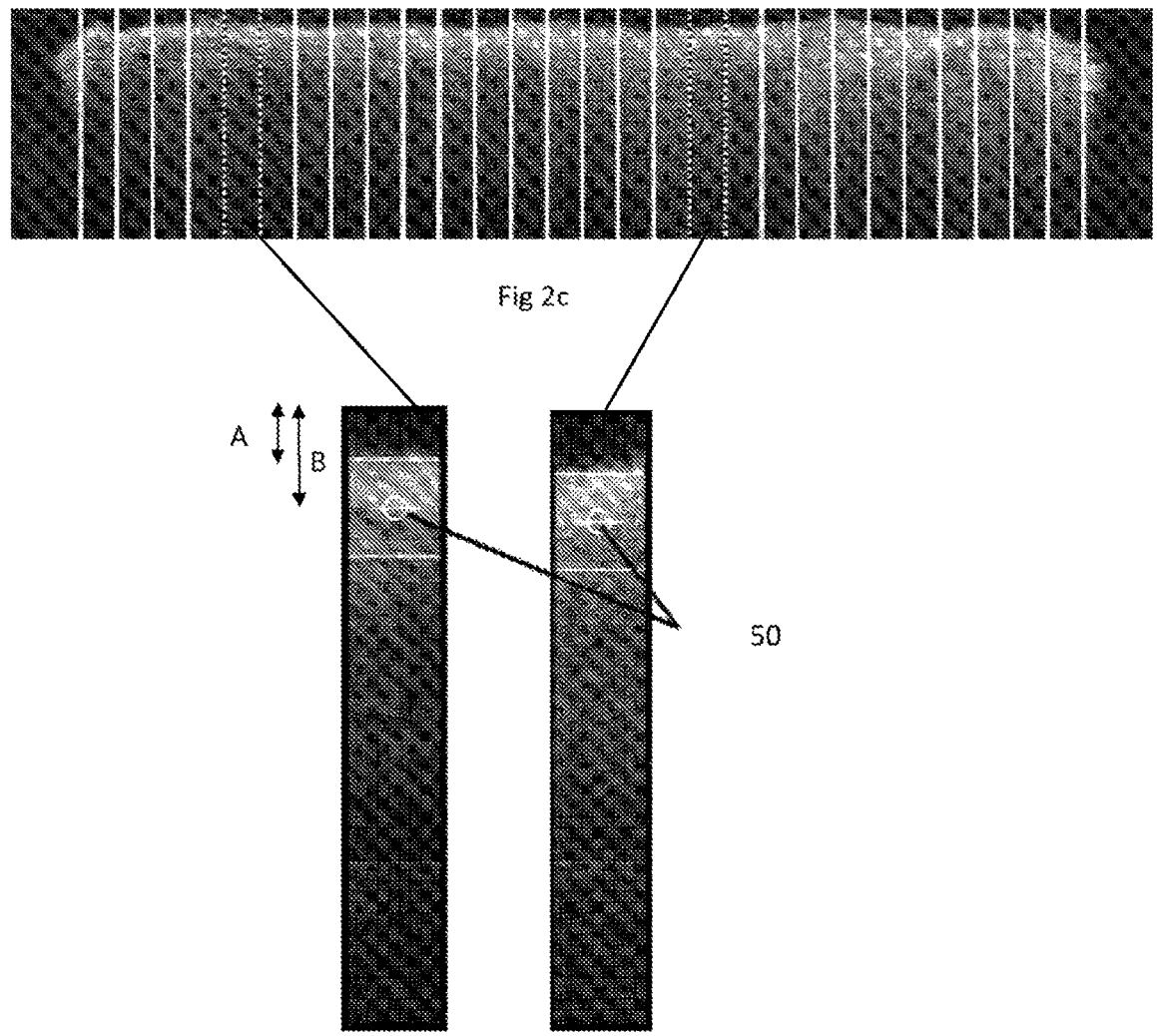
FIG. 2c shows the result of the unfolding steps in FIG. 2b.
FIG. 2d shows the detail of two sample segments from FIG. 2c

A frame which is classified as disease present may have local (finer) artefacts with potential for correction. These frames are thus processed further. The next step S108 is to reconfigure the received frame by virtually unfolding the wall vessel as illustrated schematically in FIG. 2*b*. As shown, the appearance is similar to that of opening the artery with a single longitudinal cut to unfold it flat. This reconfiguration results in a series of homogenous aligned, flat strips as illustrated in FIG. 2*c*. Accordingly, the reconfiguration may be considered to be a sampling step which samples or extracts the received frame into a plurality of samples (or strips or segments—the terms may be used interchangeably). The samples are consistently located along an aligned baseline which may be the lumen to tissue interface (i.e. the luminal edge). Each segment may be micron sized, e.g. with a width of around 80 μm. Such an alignment ensures that when a neural network receives the samples as inputs, the network may focus on the task (i.e. learning arterial disease) rather than irrelevant features, such as the OCT light receptor and its movement. At least one of the samples may then be classified as described in more detail in relation to FIGS. 3*a* to 3*h* (step S110). This local classification may include determining whether or not there are any artefacts in each sample. The sample may be classified as having no artefact, having a correctable artefact or having a non-correctable artefact. A next step may be to determine whether or not to process these frames further, i.e. to determine whether or not to measure features within the image (step S112).

These stages which remove unusable frames and/or samples may be considered to be pre-processing to clean the images. The micron-sized tissue regions of each OCT frame may then be processed as described below, for example to classify the cell wall and/or to measure the fibrous cell thickness. As illustrated, the irrelevant lumen space may be effectively discarded but the full underlying OCT resolution may be used to analyse the artery wall.

For each segment, an interface 50 between the fibrous cap tissue and the underlying layer (e.g. necrotic core or calcium) may be determined. The interface may be one feature of an individual measurement vector for each tissue component. Identification of tissue planes has previously been attempted with an edge detector. As illustrated in FIG. 2d, the left hand segment has a more defined edge than the right hand segment which appears hazy on an OCT image. Even for a more defined edge, calcium subjacent to fibrous tissue shares edge-gradient properties with internal elastic lamina, guide wires, and other artefacts and thus the edge may be incorrectly identified. Furthermore, for the segments having interfaces between fibrous tissue and lipid rich cores which lack a typical edge, edge detection may not be effective. In this method, a neural network may be used to determine the interface and other features of the vector.

For example, a neural network using a regression bounding box approach such as that described in Fast R-CNN published in 2015 by Girschick may be used to identify the interface between fibrous tissue and necrotic tissue or between fibrous tissue and calcific tissue (corresponding to soft or hard edge-gradients respectively). As explained above, all the samples (i.e. network inputs) are of the same size and the use of such image segments which are simplified when compared to the original image means that a simpler neural network may be used. For example, the neural network may have approximately 15 layers.

Referring to FIG. 2e, the distance of interest is the thickness d of the fibrous tissue under the lumen edge 10 between the fibrous tissue and the underlying layer. The fibrous tissue (i.e. the plaque region) is bounded by the lumen 10 and the interface 50 (or abluminal edge). A valid thickness was accepted for scan lines intersecting both lumen and abluminal edges around the lumen path and originating from an index position at the centre of the OCT device 14 (i.e. the centre of the light source). Such measurements emulate typical clinician measurement.

A regression network typically produces measures relative to a fixed landmark which may be selected as the top of each sample, i.e. the short edge of each sample which is closest to the lumen edge. Returning to FIG. 2d, the regression network may then measure the edge distance A from the top of the sample to the lumen edge and the interface distance B from the top of the sample to the interface 50 (or abluminal edge) between the fibrous tissue and the underlying layer. The fibrous cap thickness in pixels is estimated as the difference between the edge distance A and the interface distance B.

The pixel distance was converted to a micron distance using clinician calibration of each pullback for each equipment manufacturer to standardise output. Average cap pixel intensity was taken as the mean of the scan line vector (i.e. distance d) between lumen and tissue-interface points while edge type was an expression of each sample's classification. Diseased lumen circumference may also be calculated, e.g. by using the product of the number of diseased samples (i.e. the number of segments) identified on the frame by a dimension for each segment which may be the standard 20 pixel shortest dimension. It will be appreciated that an error of just a few pixels when calculating the difference between the two measurements would significantly influence the measurement of the fibrous thickness. Using a neural network may improve the accuracy of these measurements when compared to other known techniques.

In this way, a precise regression-measurement tool combining tissue sample classification with extrapolative mapping of tissue planes of interest may be used. The method may thus comprise measuring features of interest (step S110). Extracted regression-measures and derived metrics may include fibrous cap thickness (FCT), fibrous tissue intensity, plaque composition, lumen area and diseased lumen circumference. As shown in FIG. 1c, after the interface (or other features of interest) has been measured, the process returns to extract another input frame and repeat the extracting and correcting steps for the next frame. This may be repeated for all or just some of the frames in the complete pullback set. Frame measurement vectors may thus be concatenated for each type producing classifiable features either alone or in combination for each pullback.

FIG. 2f illustrates an average of the aligned samples which averages the samples in each frame across a region of the pullback corresponding to one lesion. FIG. 2f is an unfolded presentation of the average which is similar to that shown in FIG. 2c with the lumen edge at the top of the graph. The arrow indicates the guidewire shadow region.

FIG. 2g illustrates an attention map for the same region as FIG. 2f. Like the plot shown in FIG. 2f, the attention map may be generated by the neural network which performs the measuring step (step S114) shown in FIG. 1c. Both FIGS. 2f and 2g are examples of concatenated measure vectors.

Once all the measurements for each frame have been determined, each frame's padded measurement vector may be concatenated to produce a single input array (or pullback measurement sequence) representing valid measurements over the pullback. Each last dimension (channel) may be considered to provide a map for each individual measure type (e.g. cap thickness, cap interface type, pixel intensity). As explained above, blank inputs may be included to represent images (e.g. clean healthy images) which were not measured. As an example a recurrent neural network (RNN) was used with this considerably smaller input (relative to the full 3D pullbacks), which benefits explicitly from treating the measurements as a series. The RNN may comprise long short-term memory (LSTM) cells and may have an architecture having the same number of time steps as the number of images in the original pullback (e.g. r 270 time steps where there are 270 images) stacked three cells deep. There may also be intervening cell dropout wrapper layers and the output may be through a single dense layer.

Performance of the predictor module is likely to be most influenced by proximal lesions, as these are responsible for 70% of acute coronary events, such that distal disease will not have the same significance. This may be explained because proximal disease means a larger heart attack because more heart muscle dies and it is thought that proximal LAD lesions account for the majority of fatal coronary events. An example paper describing this issue is "Assessment of Thin-Cap Fibroatheroma Distribution in Native Coronary Arteries" by Fiiji et al published in JACC Cardiovasc. Imaging 3, 168-175 (2010).

Figure 3A:
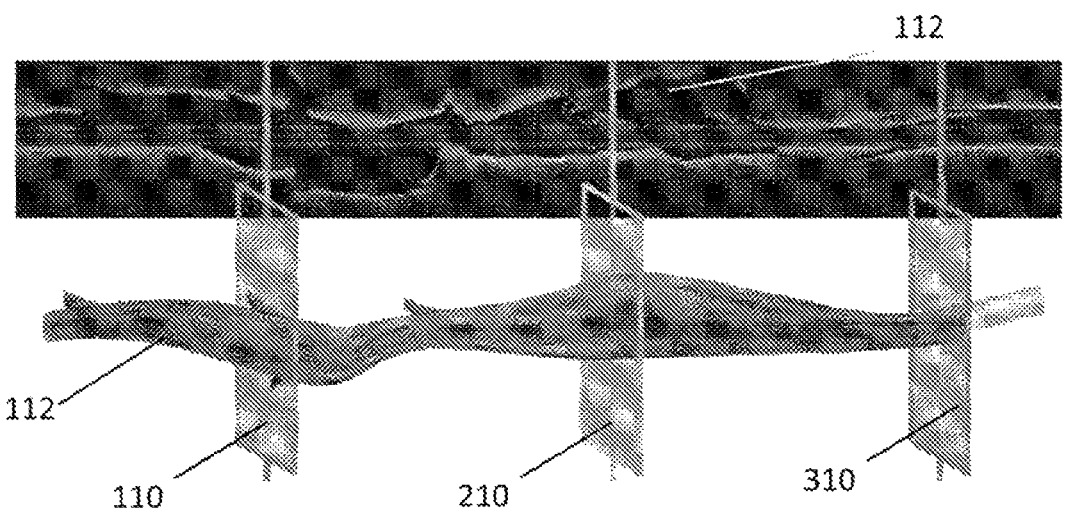
FIG. 3a is a longitudinal cross-section and a side view of an artery.
Figure 3B:
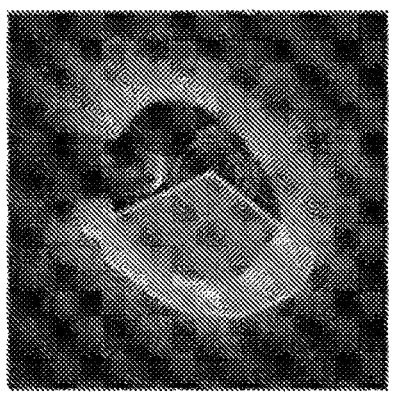
Figure 3C:
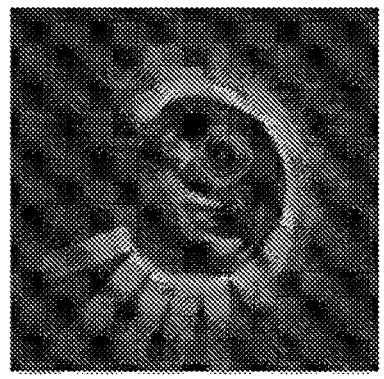

FIG. 3a shows both a cross-section image and a side view of an artery 112 with three locations of cross-section OCT images indicated. A first image 110 is taken at a location in which the artery 112 is diseased and is shown in FIG. 3b. The second image 210 is taken at a location in which there is a correctable artefact, e.g. a moderate lumen residual blood seen as a swirl which attenuates the majority of light between the 6 and 10 o'clock positions on the image shown in FIG. 3c. Correctable artefacts may result from breached intimal surfaces, focal residual lumen blood or intervening vessel walls at bifurcations and side branches which attenuate the light source and shadow adjacent tissue. Examples of such correctable artefacts are shown in FIGS. 4a to 4d. Such correctable artefacts typically constitute 0.90% of all frames in diseased segments.

Figure 3D:
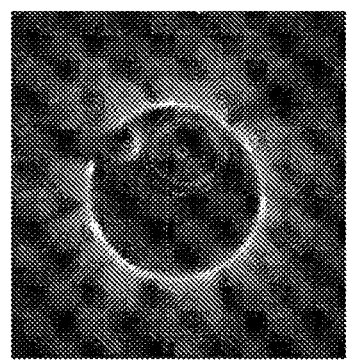

The third image 310 is taken at a location in which there is a non-correctable artefact and is shown in FIG. 3d. In this example, the non-correctable artefact includes acquisition within the guide catheter and as shown all light is attenuated by the catheter tubing. No information about the tissue outside the catheter can be obtained and thus correction is not possible because there is no data on which to base the correction. Images of non-correctable artefacts and healthy, i.e. non-diseased vessels are excluded as a first stage when correcting the artefacts.

An artefact module which includes a neural network may be used to identify and correct artefacts. The inputs may be low resolution 256×256×3 frame triplets which may be classified for presence or absence of a dominant architectural component (stent, guide catheter, branch/bifurcation), plaque type (lipid, calcific or normal vessel including intimal thickening) and luminal artefact (gross luminal residual blood and thrombus). As an example, a six layer convolutional architecture having a 7×7×3 kernel followed by 3×3×3 for every other layer may be used. The architecture may have strides of 1,2,2,1,1 and initial 64 filters, doubling the number of filters while repeating the strided spatial reduction respectively, every other layer, finishing with a fully connected layer of 1000 units. The network may be trained by supervised training for a certain number of sample frames, e.g. 300, then itself used to provisionally classify frames with subsequent re-training on those frames with corrections made to the provisional classifications.

Figure 3E:
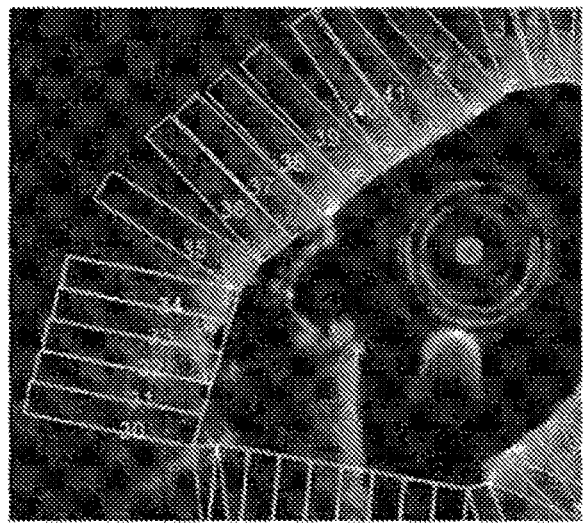
FIG. 3e is an image of an artefact showing segments.
Figure 3F:
FIGS. 3f and 3g are three segments from FIG. 3e before and after correction for an artefact.

As explained above, individual frames may be reconfigured as a plurality of samples. This is illustrated in FIG. 3e which shows how a plurality of samples (also termed window) are acquired around the lumen with their longest edge extending outwardly from lumen into the arterial wall. In this example, 20×144 pixel window may be used. These samples provide generalised training targets without loss of spatial information for later measurement. FIG. 3f shows three of these individuals which are labelled 31, 32 and 33 in FIG. 3e.

Sample artefacts are considered either correctable or non-correctable based on whether underlying tissue was detectable. For example, non-correctable samples included those where blood totally filled the lumen to attenuate all OCT signal, while focal blood shadowing or hypo-illumination typically involving less than half a sample were recoverable. Non-correctable samples often result from the presence of a stent or guide catheter at the point the image is captured. Such dominant architectural features typically result in non-correctable artefacts except in limited circumstances such as where only part of a guide catheter appears in a frame, i.e. at the guide catheter tip. To ascertain the type of artefact, for each sample which is classified as artefact present, one of 14 visually distinguishable sub-classes (as identified by the experimenter and with low feature correlation) producing consistent autoencoder latent space representations may also be used. These 14 classes correspond to the generative adversarial networks used to repair those samples as described below. As examples, the classes may be named, e.g. "include partial guidewire shadow" and "ray shadow" or may not be named but are consistently distinguishable from one another.

Where correctable artefact was present, the sample's detail was recovered with the generative arm of a variational-autoencoder generative adversarial network (VA-GAN) as described for example in "Autoencoding beyond pixels using a learned similarity metric" by Larsen et al published in 2015. Visual attribute vectors for each training sample-class were produced to add to the generators latent space, the vectors calculated as differences between the mean of all samples of the class with artefact, and the mean of every other class sample. A GAN was used to correctly reconstruct diseased targets for measurement while preserving detail and spatial resolution.

Figure 3G:
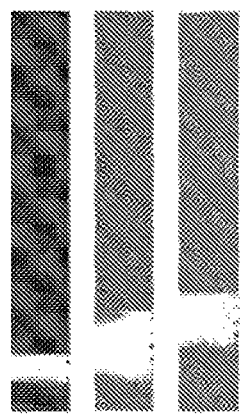
Figure 3H:
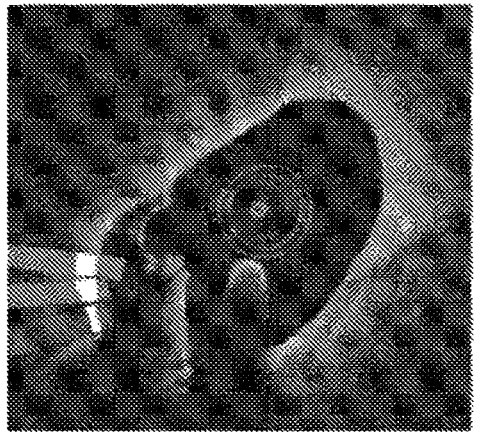
FIG. 3h is the image of FIG. 3e with the three corrected segments of FIG. 3g replacing the three segments of FIG. 3f.

FIG. 3g shows the correction of the three segments in FIG. 3f. A non-correctable artefact may be identified from a failed attempt at correction. The failure may be deduced by the output of attempted correction lacking a continuous side-to-side fibrous tissue region (for example the grey areas of FIG. 3g). Thus, each class may also have an attached binary classifier able to ascertain if correctable artefact was or was not present, i.e. to determine whether or not the correction has worked. The samples in which correction has taken place are then substituted on the original image in place of the incorrect samples as shown in FIG. 3h. The output is thus a complete image having all the samples. Multiple tissue samples such as those shown in FIG. 3e which have small individual dimensions mean the restorative results may be favourable, possibly near perfect.

Figure 4A:
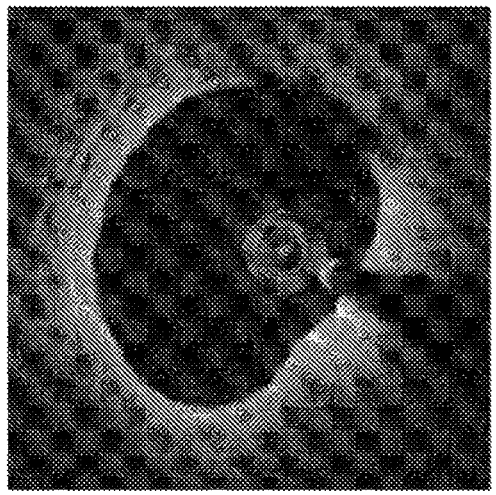
FIGS. 4a to 4d show cross-section OCT images with different types of artefact.
Figure 4B:
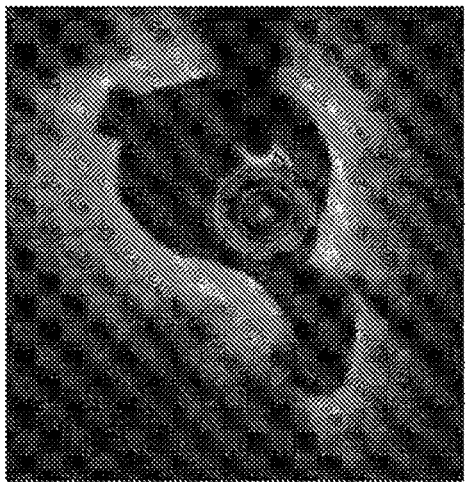
Figure 4C:
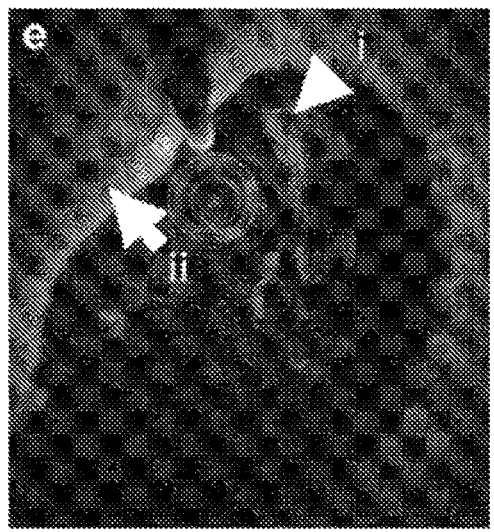
Figure 4D:
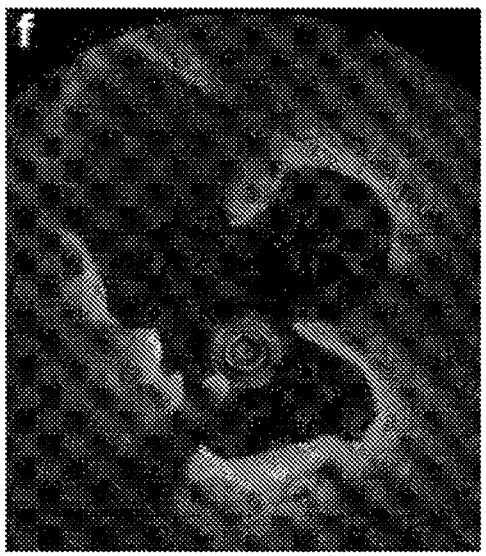

FIGS. 4a to 4d show different types of artefact. FIG. 4a shows an artefact resulting from blood and there is a shadow caused by a very small drop of unflushed blood within the OCT catheter. FIG. 4b shows an artefact caused by protrusion of the arterial wall within a side branch casting stripes of shadow below it in a 4 to 5 o'clock position. FIG. 4c is an artefact which is a combination of residual blood and bifurcation of the left main stem. Swirls of residual uncleared blood labelled (i) attenuate the signal to prevent good visualization of structures beyond. The measurable part of the diseased artery is labelled (ii). FIG. 4d is another structural artefact and there is attenuation of light at ostia of branches between left anterior descending artery, intermediate artery and circumflex artery. Removing or correcting such artefacts helps to ensure minimal feature learning based on the artefacts for training, while permitting best possible representation of the tissues for prediction.

Figure 5D:
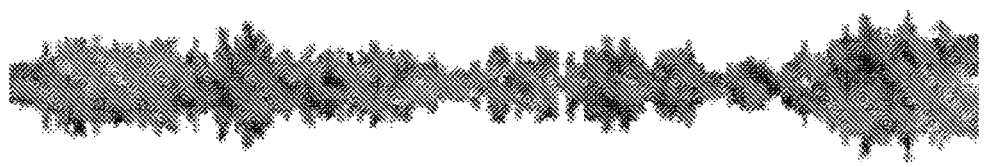
FIGS. 5d, 5e and 5f are plots of the FCT heat map along the length of the artery and aligned to a central baseline for a patient presenting with NSTEMI, STEMI and stable angina, respectively.

FIGS. 5a to 5f illustrate how the extracted features could be used in the final step of FIG. 1c to distinguish patients having stable angina from those with non ST-elevation myocardial infarction (NSTEMI) or ST-elevation myocardial infarction STEMI. FIG. 5a is a violin plot showing the number of fibrous cap thickness (FCT) measurements for patients presenting with NSTEMI and STEMI with 1 million (1e6) random samples of FCT measurements from each group for comparison. As shown, all FCT intervals occur in all patient groups. However, STEMI patients had smaller median and mean FCT measures for STEMI throughout the whole vessel. The comparisons are shown in the table below:

|  | STEMI | NSTEMI | Standard deviation (p) |
|---|---|---|---|
| Mean | 151.97 ± 26.12 | 192.41 ± 19.61 | $7.54e^{-7}$ |
| Median | 142 ± 24.5 | 183 ± 20.1 | $2.27e^{-6}$ |
| Number of measures | 1160907 | 2295090 |  |

Figure 5E:
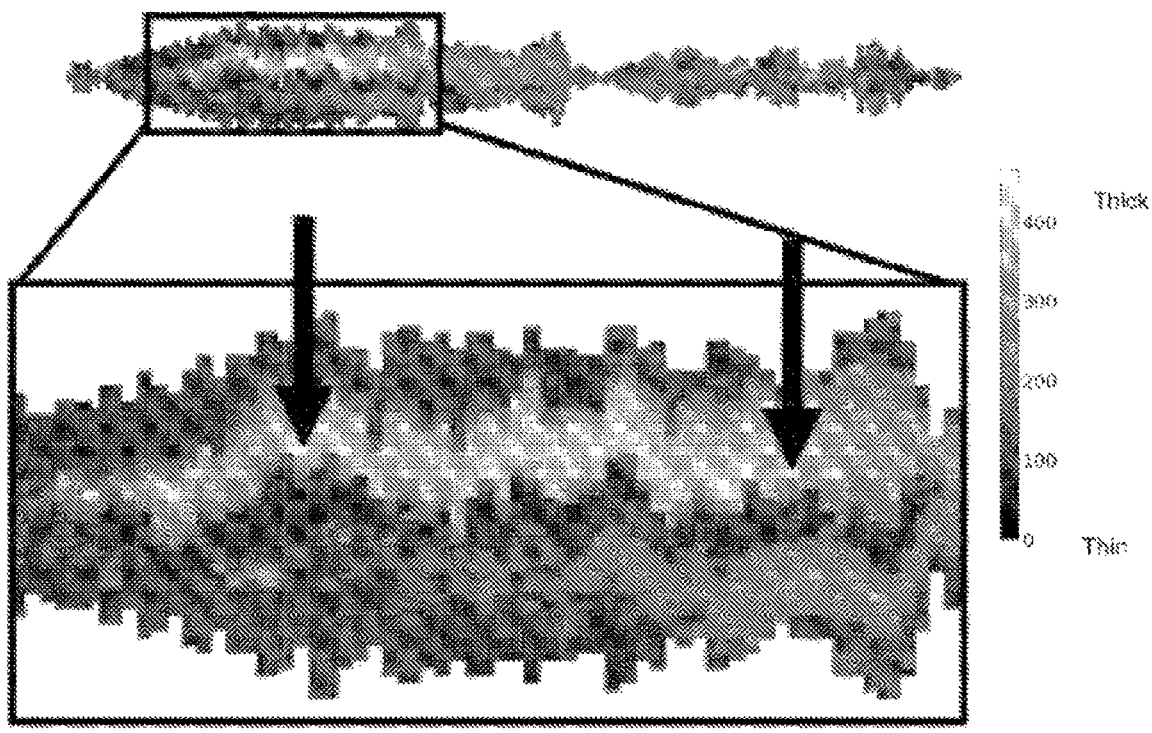
Figure 5F:

FIG. 5b is an image of a cross-section through an artery of a patient presenting with NSTEMI and FIG. 5c is an image of a cross-section through an artery of a patient presenting with STEMI. FIG. 5d is a plot of the FCT heat map along the length of the artery and aligned to a central baseline for a patient presenting with NSTEMI. The mark indicates where the image in FIG. 5*b* is captured. FIG. 5*e* is a plot of the FCT heat map along the length of the artery of a patient presenting with STEMI together with an exploded view of a sub-section. Again the mark indicates where the image in FIG. 5*c* is captured. FIG. 5*f* is a plot of the FCT heat map along the length of the artery and aligned to a central baseline for a patient with stable angina. The scale bar is in micron (μm).

As shown in FIGS. 5*d*, 5*e* and 5*f*, there are characteristic FCT patterns for each type of patient. For example, the STEMI pattern is characterised with abrupt transitions between well-demarcated thin and thick regions which may act as a focus for plaque rupture. By contrast, there are more gradual or randomly distributed FCT transitions in both NSTEMI and angina patients. In general STEMI patients also show lower FCT along the whole artery compared with NSTEMI patients not just in highly localised regions. It will be appreciated that these patterns are merely simplified examples to illustrate how the predictor module may identify types of cardiac events/disease. The RNN network chose its own features of the measurement series that best distinguished the types of cardiac events/disease. Once a patient has been diagnosed or predicted to have a particular type of cardiac disease, a method of treatment may be recommended for the patient.

Figure 6A:
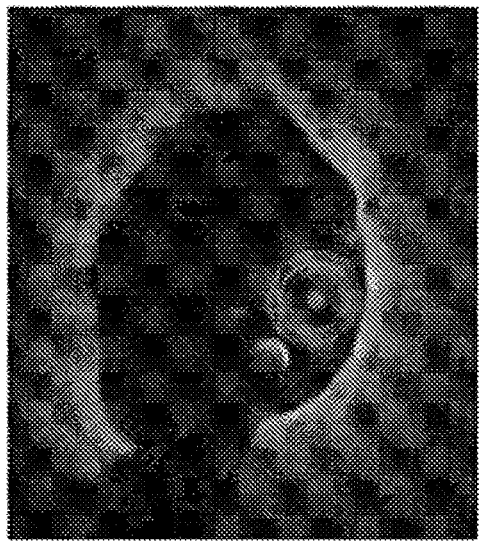
FIG. 6a shows an OCT image which was acquired post-mortem ex vivo at a point of eccentric fibroatheroma.
Figure 6B:
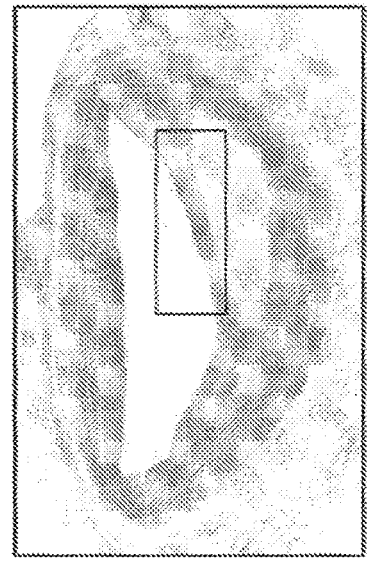
Figure 6C:
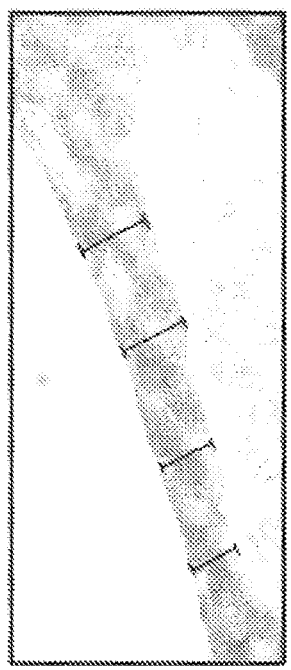
FIG. 6c is a high-power view of the area outlined in FIG. 6b.

Another prediction that may be made is to predict whether or not a patient is at high risk of sudden cardiac event. It will be appreciated that when a likelihood of death is to be predicted, the predict module will need to be trained on an appropriate dataset which includes images from patients who have died from a sudden cardiac event. As reported for example in "Vulnerable Plaque: The Pathology of Unstable Coronary Lesions" by Farb et al published in J. Interv. Cardiol. 15, 439-446 (2002), fibroatheroma cap thickness of less than 65 μm is associated with sudden cardiac death in histopathological case series. FIGS. 6*a* to 6*h* compare the performance of FCT measurements determined with FCT measurement from OCT by clinicians. The latter is challenging because of large datasets for a single artery, artefacts, and difficulties discriminating plaque from noise at the limits of resolution. FIG. 6*a* shows an OCT image which was acquired post-mortem ex vivo at a point of eccentric fibroatheroma. FIG. 6*b* is a histological section of the fibroatheroma co-registered with FIG. 6*a* and FIG. 6*c* is a high power view of the area outlined in FIG. 6*b*.

Figure 6D:
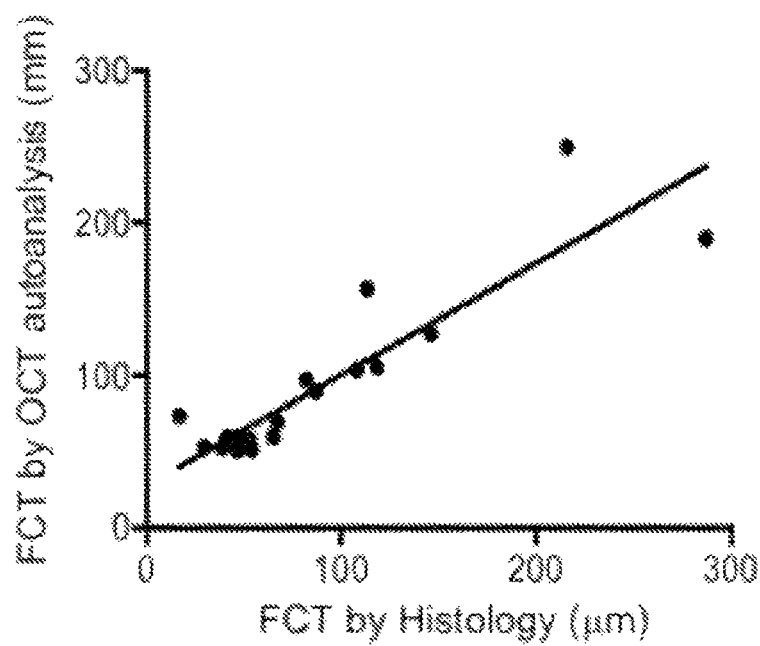
FIG. 6d plots the smallest 10 FCT measurements calculated by the method of FIG. 1c compared with the FCT measured manually on histology on co-registered slices of post-mortem ex vivo acquired OCT images.

FIG. 6*d* plots the smallest 10 FCT measurements calculated by the method described above compared with the FCT measured manually on histology on co-registered slices of post-mortem ex vivo acquired OCT images. In this example, a post-mortem dataset was collected from 14 human left anterior descending arteries. Mean patient age was 71.1±11.8 years, non-occlusive cardiovascular disease was responsible for death in 57.1% of cases with the remainder being non-cardiovascular. The study protocol was approved by Cambridgeshire Research and Ethics Committee 07/H0306/123, with informed consent from relatives. OCT was performed within 48 hours of harvesting on excised tissue collected with 40 mm of surrounding material for structural integrity, and stored in 4° C. phosphate-buffered saline. Side branches were ligated, vessels rewarmed and a guide catheter sutured into the left coronary ostium. A 0.014" Abbott Vascular BMW Universal or Pilot 50 guidewire was used for catheter delivery on a custom-built rig. OCT imaging was undertaken with saline pressure perfusion at 100 mmHg with DragonFly C7 catheters (St. Jude Medical) using a 25.0 mm/s automated pullback.

After imaging, arteries were fixed in 10% buffered formalin for 24 hours then regions of interest defined every 5 mm along the artery, and 5 μm sections taken every 400 μm and labelled maintaining lengthwise orientation with respect to the ostium. Histological sections were stained with haematoxylin-eosin and Van Gieson before being measured by two clinicians, each measure reviewed by an experienced cardiac pathologist in random order. Fibrous cap thickness was determined by thickness of a layer of smooth muscle cells infiltrated to some degree by lymphocytes or macrophages as described for example in "Lessons from sudden coronary death: a comprehensive morphological classification scheme for atherosclerotic lesions" by Virmani et al published in Arterioscler. Thromb. Vasc. Biol. 20, 1262-1275 (2000). Measurements were taken over the lipid-rich core initially, at 200 μm intervals for the circumferential distance the distinct smooth muscle plane was appreciable, including (de-)calcified areas along exactly the same plane and in contact with lipid-core. Areas representing calcification contiguous with lipid were included as between 30 and 35% of ruptures show either diffuse or fragmented calcific plates as described in "Vulnerable Plaque: The Pathology of Unstable Coronary Lesions" by Virmani et al published in J. Interv. Cardiol. 15, 439-446 (2002).

Histology was co-registered to OCT initially, to each 5 mm interval from the guide catheter to the strict corresponding distance on OCT, then at each 400 μm from that point. Each OCT frame was accompanied by two frames either side to form a triplet for comparison to histology, as discussed below, with the system rigorously observed for co-registration regardless of artefact particular to either modality. 155 (75%) of randomly selected co-registered histological sections were used to calibrate the software's measure of fibrous cap thickness and then excluded, the remainder used to form part of the validation study. No ex-vivo data was used to train the specific region of interest classifier.

Figure 6E:
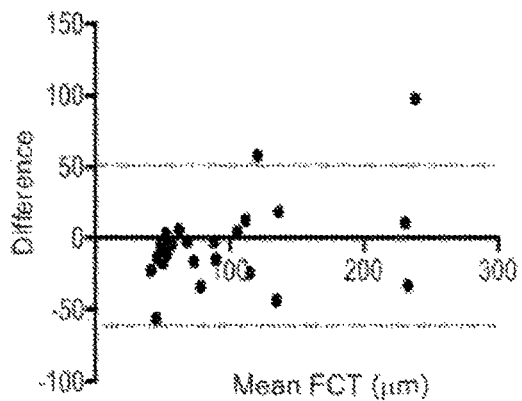
FIG. 6e is a Bland-Altman plot with varying mean FCT showing the difference between the FCT measurements calculated by the method of FIG. 1c compared with the FCT measured manually on histology.

FIG. 6*e* is a Bland-Altman plot with varying mean FCT showing the difference between the FCT measurements calculated by the method described above compared with the FCT measured manually on histology. The FCT was similar using both techniques (86.6±65.12 μm vs. 91.6±53.2 μm p=0.355), with a good correlation between measures (r=0.90, p<0.001).

Figure 6F:
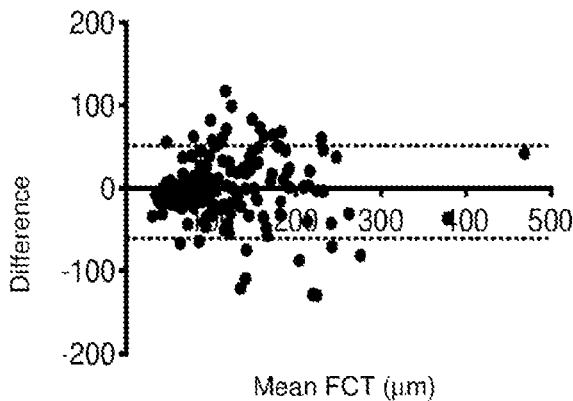
FIG. 6f is a Bland-Altman plot with varying mean FCT showing the difference between the FCT measurements calculated by the method of FIG. 1c compared with the FCT manually by independent consultant cardiologists from different centres.

FIG. 6*f* is a Bland-Altman plot with varying mean FCT showing the difference between the FCT measurements calculated by the method described above compared with the FCT manually by independent consultant cardiologists from different centres experienced in research OCT measurement using the same post-mortem frames, and 80 frames randomly selected from clinical trial patients (clinician intra-class correlation=0.84 [0.69-0.92]). Again the FCT measured automatically and manually was similar (121.8±70.4 μm vs. 124.2±74.9 μm p=0.2621). FCT measurements were validated against clinicians on OCT pullbacks from 100 separate arteries in addition to 30 OCT frames from post-mortem lesions unseen by the algorithms.

Figure 6G:
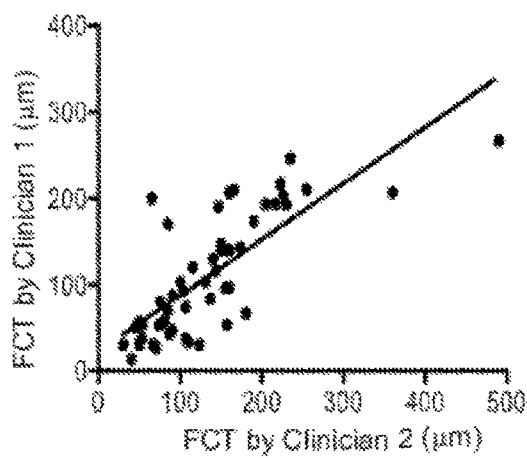
FIG. 6g plots FCT measurements from two different clinicians.

For comparison, FIG. 6*g* plots FCT measurements from two different clinicians. There is a good correlation but FCT acquired automatically using the method described above was closer to the histological FCT in 86.9% of cases.

Another prediction which could be provided by the method is the likelihood of myocardial infarction. This may result from rupture or erosion of an atherosclerotic plaque, generating post-event intraluminal features such as thrombosis and standing columns of blood. Culprit vessels are often stented, but plaques upstream and downstream of stented segments can cause further events. The method used above is context-independent because it only analyses the thickness of the fibrous cap and thus the context-independent features used by our multistage classifier may provide correction for any confounding factors.

Figure 6H:
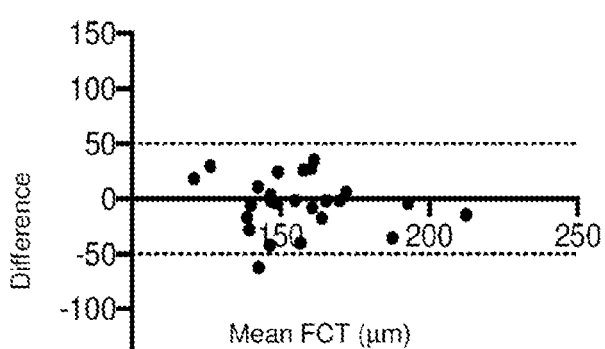
FIG. 6h is a plot showing the variation in mean FCT when the FCT measurement is taken at different times on the same day.

FIG. 6h is a plot showing the variation in mean FCT when the FCT measurement is taken at different times on the same day. Analysis of repeat pullbacks of 25 patients taken on the same day showed no significant difference between IVI2M-derived mean whole artery FCT (154.1±22.3 to 158.3±25.08 p=0.41).

Figure 7A:
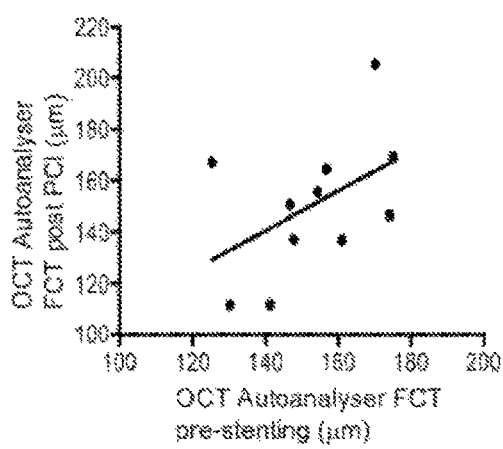
FIG. 7a plots the mean FCT measures post-stent and pre-stent.
Figure 7B:
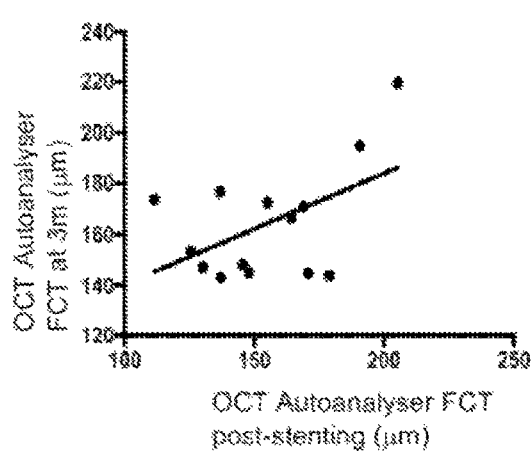
FIG. 7b plots the mean FCT measured 3 months after stenting and immediately after stenting.

FIGS. 7a and 7b examine performance of the multistage classifier in the most challenging clinical situations, including pre-stenting and post-stenting STEMI. In the case of repeatability studies performed pre-stenting and post-stenting, the stent was an everolimus-eluting bioresorbable vascular scaffold. Repeat studies of the same artery both pre- and post-stenting or post-stenting and follow up were conducted. For this comparison, 63 whole pullbacks from 18 patients (54.7±7.8 years of age, 88.8% male) planned for multi-stage OCT studies (both pre- and post-PCI and again at 3 months) were exported as individual multi-frame, lossless TIFF files, for a repeatability study. Each patient had three pullbacks, two on the same day (before and after PCI) and one at 3 months. Only images showing guide catheter and a matched portion of vessel containing stent were excluded, the latter undertaken manually by counting the number of frames showing the stented segment on the post-PCI pullback, then the number of frames to the nearest fiduciary point, determining the number of frames from the fiduciary point to the start of the stent on the pre-PCI pullback as well as the precise number of frames to exclude. Other than stented segments and guide catheter, no image exclusion regardless of severity of artefact was made.

FIG. 7a plots the mean FCT measures post-stent and pre-stent. FIG. 7b plots the mean FCT measured 3 months after stenting and immediately after stenting. The results are presented in the table below and are similar indicating the reproducibility of results using the automatic method described above:

|  | Pre-stenting | Post-stenting |  |
|---|---|---|---|
| Mean | 153.0 ± 16.7 μm | 150.6 ± 27.0 μm | p = 0.7502 |
| Minimum | 61.8 ± 8.8 μm | 66.5 ± 13.8 μm | p = 0.1833 |
| Maximum | 262.7 ± 44.0 μm | 255.1 ± 43.1 μm | p = 0.5637 |

|  | Immediately post-stenting | 3 months later |  |
|---|---|---|---|
| Mean | 155.0 ± 26.5 μm | 164.3 ± 22.7 μm | p = 0.1829 |

Figure 8:
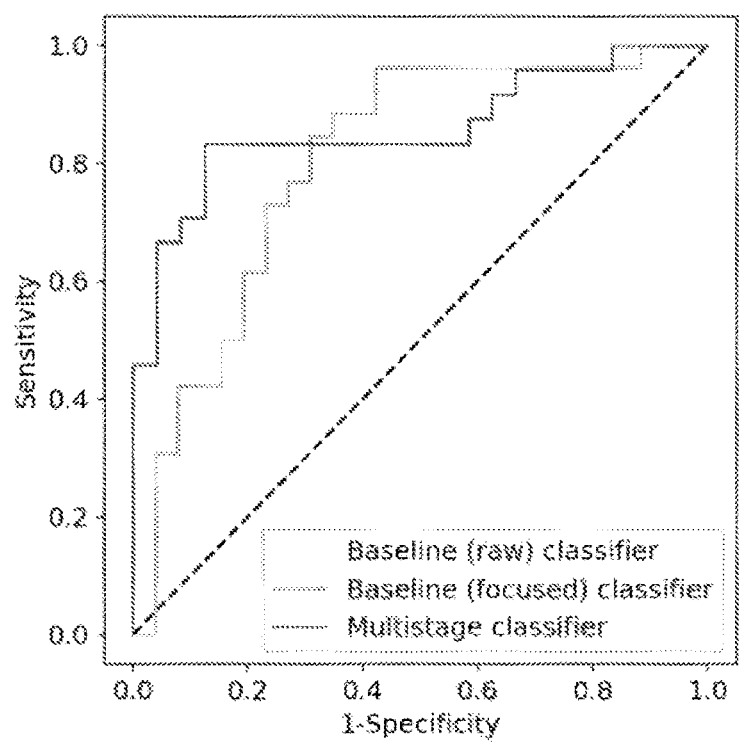
FIG. 8 plots the receiver operating curves of performance for the three classification models applied to independent non-ST elevation myocardial infarction dataset.

As described above, neural networks are used in the analysis of the OCT image. FIG. 8 compares the performance of different systems which also incorporate neural networks with the method described above in FIG. 1c. The first comparison system is termed a baseline classifier and used current state-of-the-art 3D convolutional-residual neural networks to generate classifiers of patient presentation with raw volumetric data of coronary arteries. The second comparison system is termed a focussed baseline classifier and was a two-stage network. Both classifiers were validated for patients presenting with stable angina (SA), ST elevation myocardial infarction (STEMI), and non-ST elevation myocardial infarction (NSTEMI). The multi-stage classifier was additionally validated against post-mortem, against two clinicians, and repeatability datasets. In the first stage, artefacts were identified as described above in a similar manner to that described. Correctable artefacts were corrected and non-correctable artefacts were removed. In a second stage, the remaining images were sampled and aligned as described above for consistent measurement or classification.

For each of the three methods, the training dataset (and related 10% hold-out test proportion) was from anonymised patients undergoing OCT for any reason at cardiothoracic centres based at Papworth, Brighton and Swansea hospitals, UK. There were 293,490 images taken from 1087 arteries. The multistage classifier described in FIG. 1c was additionally trained using a further 47,520 images from 176 arteries which were in a different format (Terumo). These images were only possible to use for the multistage classifier because of its modular independence at each stage. In other words, the final stage (predictor) could not know or become biased by format. Training iterations were made on 90% of the training dataset with parameter adjustment, testing and retraining on a 10% hold-out set. Artefact, region of interest and measurement algorithms were developed with 100 pullbacks (each with 270 frames) from the training dataset and updated where appropriate with histological ground truths from 14 patients undergoing post-mortem OCT.

Subsequent validation was performed on a non-ST elevation myocardial infarction (NSTEMI)/stable angina trial dataset from Ashford and St Peters Hospitals, UK, and an ST elevation myocardial infarction (STEMI)/stable angina dataset from Papworth. Stable angina patients at Ashford and St Peters Hospitals had typical symptoms present on at least two anti-ischaemia medications and lesions of >70% stenosis on separate angiography pre-dating the OCT procedure. NSTEMI was diagnosed by typical symptoms and a troponin level above the 99th percentile reference for the hospital. Recruitment was approved by Research Ethics Service Committee South East Coast-Surrey, UK (REC Reference: 13/LO/0238) and registered as clinical trial NCT02335086. Patient demographics of both validation datasets are presented below:

|  | NSTEMI/SA | STEMI/SA |
|---|---|---|
| Presentation ACS | 50% | 61% |
| Age | 62 +/− 9.52 | 69.4 +/− 11.3 |
| Smoking | 67% | 72% |
| Diabetes Mellitus | — | 20% |
| Hypertension | 48.8% | 56% |
| Previous MI | 0 | 5% |
| Previous Stent | 0 | 8% |
| Hypercholesterolaemia | 32.4% | 18% |
| Preceeding statins | — | 31% |

The results for each of the training test dataset (i.e. 10%) and the two validation datasets are compared below and in FIG. 8.

| Dataset | TRAINING DATASET | | | |
|---|---|---|---|---|
| | Sensitivity | Specificity | ACC (accuracy) | AUC (Area under curve) |
| Raw baseline classifier | 0.73 | 1.0 | 0.87 | 0.95 |
| Focused baseline classifier | 0.94 | 0.74 | 0.84 | 0.84 |
| Multistage classifier | 0.84 | 0.91 | 0.87 | 0.88 |

The accuracy may be calculated from (TP+TN)/(Real positive+Real negative) where TP is the true positive and TN is the true negative.

| Dataset | SA/NSTEMI VALIDATION DATASET | | | | STEMI/SA VALIDATION DATASET | | | |
|---|---|---|---|---|---|---|---|---|
| | Sens | Spec | ACC | AUC | Sens | Spec | ACC | AUC |
| Raw baseline classifier | 0.73 | 0.85 | 0.79 | 0.86 | 0.91 | 0.94 | 0.92 | 0.93 |
| Focused baseline classifier | 0.88 | 0.65 | 0.77 | 0.8 | 0.88 | 0.58 | 0.73 | 0.74 |
| Multistage classifier | 0.83 | 0.75 | 0.79 | 0.87 | 0.86 | 1.0 | 0.92 | 0.99 |

Good baseline performance is observed with the raw baseline classifier (AUC 0.86, ACC 0.79, sensitivity 0.73). However, analysis demanded impractical computing resources to train in view of instance sizes (512×512×256). Furthermore, the classifier's emphasis on unamended raw frame analysis meant that it lacked ability to disregard a range of OCT artefacts. Such major artefacts (defined as diffuse intra-luminal artefact attenuating signal) were significantly higher in myocardial infarction than angina patients (40.2% v 38.1% p=0.0333).

The focused baseline classifier improved sensitivity (0.88) on the independent NSTEMI/stable angina dataset compared to the baseline classifier, while requiring less training data augmentation (2934 vs. 9783 artery examples produced through standard distortions, i.e. rotation or flipping, brightness adjustment). For the multistage classifier described in FIG. 1c, inputs containing fibrous cap thickness were found to be best on the NSTEMI validation dataset (AUC 0.87, ACC 0.79, and sensitivity 0.83).

Performance of the multistage deep-learning-based classifier was also compared with that of conventional machine learning algorithms, including K-nearest neighbours, Random Forest, and support vector machines, using both the frame images and panels of discrete features and attributions with random searches for optimal hyper-parameters. The best conventional algorithm (Random Forest) performed only moderately well against the first (NSTEMI/SA) validation dataset (AUC 0.74, sensitivity 0.74, specificity 0.6), with the best estimators arising with inputs of FCT intervals between 140 μm and 220 μm.

For completeness, the details of each of the training datasets and validation datasets are summarised in the table below (where n is the number of arteries, and i is the number of OCT images). As mentioned above, both classifiers were validated for patients presenting with stable angina (SA), ST elevation myocardial infarction (STEMI), and non-ST elevation myocardial infarction (NSTEMI). The multi-stage classifier was additionally validated using ex-vivo post-mortem pullbacks correlated with histology, comparison with two clinician observers, and repeatability studies on the same day.

| | Baseline classifier | Focussed baseline classifier | Multi-stage classifier |
|---|---|---|---|
| Training dataset | n = 1087, i = 293,490 | n = 1087, i = 293,490 | n = 1,263, i = 341,010 |
| NSTEMI validation | n = 52, i = 14,040 | n = 52, i = 14,040 | n = 52, i = 14,040 |
| STEMI validation | n = 38, i = 10,260 | n = 38, i = 10,260 | n = 38, i = 10,260 |
| Post mortem | | | n = 22, i = 5,940 |
| Clinician | | | n = 114, i = 330 |
| Repeatability | | | n = 25, i = 5,670 |

As mentioned above, intracoronary images could be analysed to predict the likelihood of a disease or event, and/or to track performance of a drug or other treatment. Coronary artery disease (CAD) imaging has the potential to identify high-risk plaques and is a widely used surrogate efficacy marker for Phase 2/3 drug studies. However, event rates of presumed 'high-risk' lesions identified using different imaging modalities are below those needed to change management of individual plaques. Intracoronary optical coherence tomography (OCT) produces very high-resolution sequences that can provide exquisitely detailed plaque images. Furthermore, a number of OCT parameters are associated with high-risk lesions, including: minimum fibrous cap thickness FCT (<75 μm), minimum lumen area (MLA)<3.5 $mm^2$, lipid pool extension inside plaque>180°, and presence of macrophages, calcific nodules, neovascularization, or cholesterol crystals. Some of these OCT features change with treatment with high-dose statins or ezetimibe, suggesting that they may indicate plaque stabilization. However, OCT pullbacks are rich datasets containing hundreds of images and tens-of-thousands of candidate measurements per artery. Consequently, OCT analysis currently requires time-consuming offline manual frame selection and measurement in specialized core laboratories, and is limited by inter- and intra-observer variability. Fully automated measurement is also limited by high frequency of artefacts, and similarity of artefact to disease. Thus, the present OCT autoanalysis system/methods could be used to by clinicians and industry to measure disease progression/instability and discriminate different presentations with CAD to allow more cost-effective patient management.

The present OCT autoanalysis system/method was used to analyse the efficacy of a particular treatment, specifically that of a treatment of Rosuvastatin. Images were captured at baseline (pre-treatment) and after 13m of 40 mg Rosuvastatin treatment.

Currently optical coherence tomography (OCT) is rarely used to examine the efficacy of anti-atherosclerosis drugs, in part because of the extensive and partly manual selection and offline analysis of baseline and follow-up images, limiting analysis to small numbers of frames. In contrast, the present OCT autoanalysis method's fully automated analysis can generate whole plaque circumferential FCT maps comprising thousands of individual FCT measurements ($2.0 \times 10^3$-$1.0 \times 10^6$ measurements/artery, median $4.1 \times 10^4$), and examine other features associated with plaque stability such as lipid content or calcification based on pixel gradients between fibrous and subjacent tissue.

The study examined non-culprit artery lesions at baseline and after 13m of 40 mg/day Rosuvastatin treatment. FCT was measured from manually selected frames and measured semi-automatically in 31 lesions from 27 patients. In the original analysis minimum FCT increased, both macrophage line arc and mean lipid arc decreased, and 9/13 thin cap fibroatheromas (TCFAs) regressed to non-TCFA morphology. The present OCT autoanalysis method enabled examination of both plaque and whole vessel appearances at baseline and follow-up of 83 patients without manual selection of frames. There was a significant increase in whole plaque mean FCT (161.98±44.91 µm vs. 183.99±46.18 µm p=0.0038) at follow-up, despite no change in lumen surface area covered by lesions (181.68±163.72 mm$^2$ vs. 223.37±199.86 mm$^2$, p=0.163). Minimum FCT/frame also showed a significant increase at follow up (83.39±29.87 µm vs. 98.29±41.00 µm, p=0.0113), while 63.37% of individual frames (95% confidence interval (CI) 59.88-67.58) showed an increase in FCT at follow-up.

To determine the effects of high intensity statin on the smallest FCT, whole artery FCT counts/artery were examined at different FCT thresholds.

FIG. 9a shows boxplots of measurement frequency of FCT at different thickness thresholds (75 µm and 65 µm) between a pre-treatment baseline and post-treatment follow-up (at 13m). Data are median, and error bars represent the 25% and 75% quartiles. Although whole artery counts of FCT, lipid or calcium vary considerably between arteries, in large part because of differing plaque burden, there was a significant reduction in the number of points where cap thickness was smallest (<65 µm (85540 vs. 87731 (no of points) or 1.9% vs. 2.1% (% of all measures), p<0.0001), suggesting that rosuvastatin has the greatest effect on the thinnest fibrous caps.

FIG. 9b shows a single patient's frame-wise plots of FCT between the pre-treatment baseline and post-treatment follow-up. The varying line represents mean FCT for each frame, while the constant horizontal line represents the mean FCT for whole pullback. The arrows indicate the same point along the patient's artery, showing regression of a thin cap region (i.e. thickening of the fibrous cap). It can be seen from FIG. 9b that the multi-stage classifier also allows direct comparison of FCT plots along the whole plaque at baseline and follow up, which revealed the plaque regions where FCT increases or decreases.

FIGS. 9c and 9d show, respectively a boxplot of frequency of lipid between the pre-treatment baseline and post-treatment follow-up and a boxplot of frequency of calcification between the pre-treatment baseline and post-treatment follow-up. It can be seen from FIGS. 9c and 9d that there was also a small but significant reduction in the proportion of lipid from 20.00% at baseline to 18.06% at follow up (p<0.0025) and increase in calcium (from 24588 vs. 38105 (no of points) or 3.1% vs. 4.9% (% of all measures), p=0.016) at the whole artery level. Thus, it can be seen that the present OCT autoanalysis method can be used to monitor the efficacy of anti-atherosclerosis therapies and prediction of patient events.

At least some of the example embodiments described herein may be constructed, partially or wholly, using dedicated special-purpose hardware. Terms such as 'component', 'module' or 'unit' used herein may include, but are not limited to, a hardware device, such as circuitry in the form of discrete or integrated components, a Field Programmable Gate Array (FPGA) or Application Specific Integrated Circuit (ASIC), which performs certain tasks or provides the associated functionality. In some embodiments, the described elements may be configured to reside on a tangible, persistent, addressable storage medium and may be configured to execute on one or more processors. These functional elements may in some embodiments include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. Although the example embodiments have been described with reference to the components, modules and units discussed herein, such functional elements may be combined into fewer elements or separated into additional elements. Various combinations of optional features have been described herein, and it will be appreciated that described features may be combined in any suitable combination. In particular, the features of any one example embodiment may be combined with features of any other embodiment, as appropriate, except where such combinations are mutually exclusive. Throughout this specification, the term "comprising" or "comprises" means including the component(s) specified but not to the exclusion of the presence of others.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. An automated computer-implemented method for analysing a set of images of a coronary artery, the method comprising:
    for each image in the set of images:
    classifying the image, using a first neural network, for the presence or absence of diseased tissue;
    when the image is classified as having diseased tissue present, classifying the image, using a second neural network, for the presence or absence of an artefact;
    determining whether to analyse the image based on the classifying steps;
    when the image is to be analysed, analysing the image by identifying, using a third neural network, one or more features of interest in a coronary artery tissue; and
    measuring each identified feature of interest,
    wherein the method comprises an initial frame wise classification of the image, wherein the initial frame wise classification provides screening to identify at least one dominant component which causes false measurements, and wherein the set of images comprises a first subset of images of the coronary artery of a patient captured at a first time and a second subset of images of the coronary artery of the patient at a second, subsequent time, and the method further comprises:

measuring a first set of measurements for each identified feature of interest for the first subset of images;

measuring a second set of measurements for each identified feature of interest for the second subset of images; and determining, using the first and second sets of measurements, any change in the coronary artery.

2. The method as claimed in claim 1, further comprising, prior to classifying the image using the second neural network, sampling the coronary artery in the image into a plurality of samples and inputting a set of samples into the second neural network.

3. The method as claimed in claim 2, wherein classifying the image comprises:

determining a proportion of coronary artery tissue which is detectable in each sample in the input set; and classifying the image based on the determined proportion.

4. The method as claimed in claim 2, further comprising: training the second neural network to classify the image by analysing a plurality of training dataset samples.

5. The method as claimed in claim 2, wherein when an image is classified as having an artefact present, further classifying the artefact as correctable or non-correctable.

6. The method as claimed in claim 5, wherein classifying the image comprises:

determining a proportion of coronary artery tissue which is detectable in each sample in the input set; and classifying the image based on the determined proportion, and wherein the image is classified as having a correctable artefact when the determined proportion is over 50%.

7. The method as claimed in claim 5, comprising, prior to analysing the image, correcting the image which has been classified as having a correctable artefact, preferably wherein correcting an image classified as having a correctable artefact comprises applying a variational-autoencoder generative adversarial network to the identified image to recover detail of the coronary artery tissue underneath the identified artefact.

8. The method as claimed in claim 1, wherein when the image is classified as having an absence of diseased tissue, replacing the image with blank information; and/or wherein measuring each identified feature of interest comprises measuring any one or more of: fibrous tissue thickness, fibrous tissue intensity, plaque composition, lumen area, and diseased lumen circumference.

9. The method as claimed in claim 1, further comprising, prior to analysing the image, sampling the coronary artery in the retained image into a plurality of samples; and arranging the samples in a linear representation of the coronary artery, preferably wherein analysing the image further comprises: identifying, using a regression bounding box technique, an interface between fibrous tissue and necrotic or calcific tissue in each of the plurality of samples, and further preferably wherein measuring the identified feature of interest comprises measuring the distance between the interface and an edge of the sample.

10. The method as claimed in claim 1, wherein the set of images of coronary arteries are optical coherence tomography images.

11. The method as claimed in claim 1 wherein each image is of a coronary artery of a patient, and the method further comprises:

determining, using the measurement of each identified feature of interest, the likelihood of the patient having presenting with a particular manifestation of coronary artery disease.

12. The method as claimed in claim 11, determining the likelihood of the patient presenting with a particular manifestation of coronary artery disease comprises using a fourth neural network.

13. The method as claimed in claim 12, the fourth neural network receives as inputs the measurement of each identified feature of interest for each analysed image and blank information for each image which is not analysed.

14. The method as claimed in claim 11, wherein the coronary artery disease is myocardial infarction and the identified feature of interest is fibrous tissue thickness.

15. The method as claimed in claim 1, wherein the first time is a first stage in treatment and the second time is a second stage in the treatment and further comprising determining the efficacy of the treatment based on any determined change.

16. A non-transitory data carrier carrying code which, when implemented on a processor, causes the processor to carry out the method of claim 1.

17. An apparatus for analysing a set of images of a coronary artery, the apparatus comprising:

an imaging device for capturing a set of images of a coronary artery; and at least one processor, coupled to memory, arranged to: for each image in the set of images:

classify the image, using a first neural network, for the presence or absence of diseased tissue;

when the image is classified as having diseased tissue present, classifying the image, using a second neural network, for the presence or absence of an artefact;

determine whether to analyse the image based on the classifying; and when the image is analysed:

analyse the retained image, using a third neural network, by identifying one or more features of interest in a coronary artery tissue; and measuring each identified feature of interest, wherein the apparatus is configured to perform an initial frame wise classification of the image using a framewise module, wherein the initial frame wise classification provides screening to identify at least one dominant component which causes false measurements, and wherein the set of images comprises a first subset of images of the coronary artery of a patient captured at a first time and a second subset of images of the coronary artery of the patient at a second, subsequent time, and the method further comprises:

measuring a first set of measurements for each identified feature of interest for the first subset of images;

measuring a second set of measurements for each identified feature of interest for the second subset of images; and determining, using the first and second sets of measurements, any change in the coronary artery.

18. The apparatus as claimed in claim 17, wherein the imaging device is an optical coherence tomography device.

* * * * *